US012193719B2

(12) United States Patent
Edidin

(10) Patent No.: US 12,193,719 B2
(45) Date of Patent: Jan. 14, 2025

(54) MODULATING NERVES WITHIN BONE

(71) Applicant: Relievant Medsystems, Inc., Minneapolis, MN (US)

(72) Inventor: Avram Allan Edidin, Portola Valley, CA (US)

(73) Assignee: Relievant Medsystems, Inc., Redwood City, CA (US)

( * ) Notice: Subject to any disclaimer, the term of this patent is extended or adjusted under 35 U.S.C. 154(b) by 297 days.

(21) Appl. No.: 17/378,457

(22) Filed: Jul. 16, 2021

(65) Prior Publication Data

US 2021/0369323 A1  Dec. 2, 2021

Related U.S. Application Data

(63) Continuation of application No. 16/661,271, filed on Oct. 23, 2019, now Pat. No. 11,065,046, which is a (Continued)

(51) Int. Cl.
*A61B 18/14* (2006.01)
*A61B 18/04* (2006.01)
(Continued)

(52) U.S. Cl.
CPC .... *A61B 18/04* (2013.01); *A61B 2018/00339* (2013.01); *A61B 2018/00434* (2013.01);
(Continued)

(58) Field of Classification Search
CPC ......... A61B 18/04; A61B 18/12; A61B 18/02; A61B 18/08; A61B 18/14; A61B 18/1402; A61B 18/1487; A61B 18/148; A61B 18/1482; A61B 2018/00339; A61B 2018/00434; A61B 2018/00565; A61B 2018/00577; A61B 2018/00005;
(Continued)

(56) References Cited

U.S. PATENT DOCUMENTS 3,054,881 A   9/1962  Metz et al.
3,062,876 A   11/1962 Pons, Jr. et al.
(Continued)

FOREIGN PATENT DOCUMENTS

AU   2001033279   2/2001
AU   2003248436   9/2003
(Continued)

OTHER PUBLICATIONS

U.S. Appl. No. 09/775,137 U.S. Pat. No. 6,699342, filed Feb. 1, 2001, Methods and Devices Fm intraosseous News Ablation.
(Continued)

*Primary Examiner* — Thomas A Giuliani
(74) *Attorney, Agent, or Firm* — Nelson Mullins Riley & Scarborough LLP

(57) ABSTRACT

Methods of using hardware (e.g., bone screws, anchors or other devices) previously inserted within the body to facilitate energy delivery are disclosed. The energy delivery (e.g., thermal energy) may be used for neuromodulation (such as stimulation or denervation), tissue heating and ablation, curing, and other applications in the spine and non-spine orthopedic locations.

18 Claims, 2 Drawing Sheets

Related U.S. Application Data continuation of application No. 15/669,292, filed on Aug. 4, 2017, now Pat. No. 10,456,187, which is a continuation of application No. 14/454,643, filed on Aug. 7, 2014, now Pat. No. 9,724,151.

(60) Provisional application No. 61/863,821, filed on Aug. 8, 2013.

(51) Int. Cl.
  *A61B 18/00* (2006.01)
  *A61B 18/12* (2006.01)

(52) U.S. Cl.
  CPC ............... *A61B 2018/00565* (2013.01); *A61B 2018/00577* (2013.01); *A61B 18/12* (2013.01)

(58) Field of Classification Search
  CPC ...... A61B 2018/0044; A61B 2018/126; A61B 2018/1475
  USPC ............... 606/20, 21, 27–31, 41, 42, 48, 50; 607/96, 98, 99, 101, 104, 113, 115, 116
  See application file for complete search history.

(56) References Cited

U.S. PATENT DOCUMENTS

| | | |
|---|---|---|
| 3,565,062 A | 2/1971 | Kuris |
| 3,822,708 A | 7/1974 | Zilber |
| 3,845,771 A | 11/1974 | Vise |
| 3,920,021 A | 11/1975 | Hiltebrandt |
| 3,938,502 A | 2/1976 | Bom |
| 3,977,408 A | 8/1976 | MacKew |
| 4,044,774 A | 8/1977 | Corgin et al. |
| 4,116,198 A | 9/1978 | Roos |
| 4,311,154 A | 1/1982 | Sterzer et al. |
| 4,312,364 A | 1/1982 | Convert et al. |
| 4,378,806 A | 4/1983 | Henley-Cohn |
| 4,448,198 A | 5/1984 | Turner |
| 4,449,528 A | 5/1984 | Auth et al. |
| 4,462,408 A | 7/1984 | Silverstein et al. |
| 4,528,979 A | 7/1985 | Marchenko et al. |
| 4,530,360 A | 7/1985 | Duarte |
| 4,541,423 A | 9/1985 | Barber |
| 4,569,351 A | 2/1986 | Tang |
| 4,573,448 A | 3/1986 | Kambin |
| 4,586,512 A | 5/1986 | Do-Huu |
| 4,601,296 A | 7/1986 | Yerushalmi |
| 4,612,940 A | 9/1986 | Kasevich et al. |
| 4,657,017 A | 4/1987 | Sorochenko |
| 4,662,383 A | 5/1987 | Sogawa et al. |
| 4,671,293 A | 6/1987 | Shaulov |
| 4,676,258 A | 6/1987 | Inokuchi et al. |
| 4,679,561 A | 7/1987 | Doss |
| 4,681,122 A | 7/1987 | Winters et al. |
| 4,750,499 A | 6/1988 | Hoffer |
| 4,754,757 A | 7/1988 | Feucht |
| 4,757,820 A | 7/1988 | Itoh |
| 4,774,967 A | 10/1988 | Zanakis et al. |
| 4,800,899 A | 1/1989 | Elliott |
| 4,813,429 A | 3/1989 | Eshel et al. |
| 4,841,977 A | 6/1989 | Griffith et al. |
| 4,907,589 A | 3/1990 | Cosman |
| 4,924,863 A | 5/1990 | Sterzer |
| 4,936,281 A | 6/1990 | Stasz |
| 4,941,466 A | 7/1990 | Romano |
| 4,950,267 A | 8/1990 | Ishihara et al. |
| 4,951,677 A | 8/1990 | Crowley et al. |
| 4,955,377 A | 9/1990 | Lennox et al. |
| 4,959,063 A | 9/1990 | Kojima |
| 4,961,435 A | 10/1990 | Kitagawa et al. |
| 4,963,142 A | 10/1990 | Loertscher |
| 4,966,144 A | 10/1990 | Rochkind et al. |
| 4,967,765 A | 11/1990 | Turner et al. |
| 4,976,711 A | 12/1990 | Parins et al. |
| 4,977,902 A | 12/1990 | Sekino et al. |
| 5,000,185 A | 3/1991 | Yock |
| 5,002,058 A | 3/1991 | Marinelli |
| 5,002,059 A | 3/1991 | Crowley et al. |
| 5,007,437 A | 4/1991 | Sterzer |
| 5,025,778 A | 6/1991 | Silverstein et al. |
| 5,031,618 A | 7/1991 | Mullet |
| 5,061,266 A | 10/1991 | Hakky |
| 5,070,879 A | 12/1991 | Herres |
| RE33,791 E | 1/1992 | Carr |
| 5,078,736 A | 1/1992 | Behl |
| 5,080,660 A | 1/1992 | Buelna |
| 5,084,043 A | 1/1992 | Hertzmann et al. |
| 5,090,414 A | 2/1992 | Takano |
| 5,098,431 A | 3/1992 | Rydell |
| 5,106,376 A | 4/1992 | Mononen et al. |
| 5,108,404 A | 4/1992 | Scholten et al. |
| 5,131,397 A | 7/1992 | Crowley |
| 5,147,355 A | 9/1992 | Cravalho et al. |
| 5,156,157 A | 10/1992 | Nappholz et al. |
| 5,158,536 A | 10/1992 | Sekins et al. |
| 5,161,533 A | 11/1992 | Prass et al. |
| 5,167,231 A | 12/1992 | Matsui |
| 5,186,177 A | 2/1993 | O'Donnell et al. |
| 5,190,540 A | 3/1993 | Lee |
| 5,190,546 A | 3/1993 | Jervis |
| 5,201,729 A | 4/1993 | Hertzmann et al. |
| 5,207,672 A | 5/1993 | Martinelli et al. |
| 5,209,748 A | 5/1993 | Daikuzono |
| 5,222,953 A | 6/1993 | Dowlatshahi |
| 5,226,430 A | 7/1993 | Bourgelais et al. |
| 5,242,439 A | 9/1993 | Larsen et al. |
| 5,255,679 A | 10/1993 | Imran |
| 5,271,408 A | 12/1993 | Breyer et al. |
| 5,273,026 A | 12/1993 | Wilk |
| 5,281,213 A | 1/1994 | Milder et al. |
| 5,281,215 A | 1/1994 | Milder |
| 5,282,468 A | 2/1994 | Klepinski |
| 5,292,321 A | 3/1994 | Lee |
| 5,295,484 A | 3/1994 | Hynynen et al. |
| 5,300,085 A | 4/1994 | Yock |
| 5,304,214 A | 4/1994 | DeFord et al. |
| 5,305,756 A | 4/1994 | Entrekin et al. |
| 5,314,463 A | 5/1994 | Camps et al. |
| 5,320,617 A | 6/1994 | Leach |
| 5,324,255 A | 6/1994 | Gesswein et al. |
| 5,325,860 A | 7/1994 | Seward et al. |
| 5,342,292 A | 8/1994 | Nita et al. |
| 5,342,357 A | 8/1994 | Nardella |
| 5,342,409 A | 8/1994 | Mullett |
| 5,344,435 A | 9/1994 | Schaefermeyer et al. |
| 5,345,940 A | 9/1994 | Seward et al. |
| 5,348,554 A | 9/1994 | Imran et al. |
| 5,350,377 A | 9/1994 | Winston et al. |
| 5,351,691 A | 10/1994 | Brommersma |
| 5,366,443 A | 11/1994 | Eggers et al. |
| 5,366,490 A | 11/1994 | Edwards et al. |
| 5,368,031 A | 11/1994 | Cline et al. |
| 5,368,035 A | 11/1994 | Crowley et al. |
| 5,368,557 A | 11/1994 | Mills et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Abele et al. |
| 5,374,265 A | 12/1994 | Sand |
| 5,383,876 A | 1/1995 | Nardella |
| 5,385,148 A | 1/1995 | Jackson et al. |
| 5,385,544 A | 1/1995 | Edwards et al. |
| 5,391,197 A | 2/1995 | Burdette et al. |
| 5,391,199 A | 2/1995 | Ben-Haim |
| 5,405,376 A | 4/1995 | Mulier et al. |
| 5,411,527 A | 5/1995 | Alt |
| 5,417,719 A | 5/1995 | Hull et al. |
| 5,419,767 A | 5/1995 | Eggers et al. |
| 5,421,338 A | 6/1995 | Crowley et al. |
| 5,423,811 A | 6/1995 | Imran et al. |
| 5,431,649 A | 7/1995 | Muller et al. |
| 5,433,739 A | 7/1995 | Sluijter et al. |
| D361,555 S | 8/1995 | Bettin et al. |

(56) References Cited

U.S. PATENT DOCUMENTS

| | | |
|---|---|---|
| 5,437,661 A | 8/1995 | Rieser |
| 5,441,499 A | 8/1995 | Fritzsch |
| 5,441,527 A | 8/1995 | Erickson et al. |
| 5,443,463 A | 8/1995 | Stern et al. |
| 5,447,509 A | 9/1995 | Mills et al. |
| 5,449,380 A | 9/1995 | Chin |
| 5,454,373 A | 10/1995 | Crowley |
| 5,458,596 A | 10/1995 | Lax et al. |
| 5,458,597 A | 10/1995 | Edwards et al. |
| 5,471,988 A | 12/1995 | Fujio et al. |
| 5,472,441 A | 12/1995 | Edwards et al. |
| 5,474,530 A | 12/1995 | Gesswein et al. |
| 5,484,432 A | 1/1996 | Sand |
| 5,486,170 A | 1/1996 | Winston et al. |
| 5,501,703 A | 3/1996 | Holsheirner et al. |
| 5,505,730 A | 4/1996 | Edwards |
| 5,514,130 A | 5/1996 | Baker |
| 5,524,624 A | 6/1996 | Tepper et al. |
| 5,526,815 A | 6/1996 | Granz et al. |
| 5,529,580 A | 6/1996 | Hagino et al. |
| 5,540,679 A | 7/1996 | Bems et al. |
| 5,540,681 A | 7/1996 | Strul et al. |
| 5,540,684 A | 7/1996 | Hassler, Jr. |
| 5,545,161 A | 8/1996 | Imran |
| 5,560,362 A | 10/1996 | Curley et al. |
| 5,565,005 A | 10/1996 | Bettin et al. |
| 5,569,242 A | 10/1996 | Lax et al. |
| 5,571,088 A | 11/1996 | Beaudet et al. |
| 5,571,147 A | 11/1996 | Sluijter et al. |
| 5,575,772 A | 11/1996 | Lennox |
| 5,575,788 A | 11/1996 | Baker et al. |
| 5,588,432 A | 12/1996 | Crowley |
| 5,596,988 A | 1/1997 | Markle et al. |
| 5,601,526 A | 2/1997 | Blanc et al. |
| 5,606,974 A | 3/1997 | Castellano et al. |
| 5,609,151 A | 3/1997 | Mulier et al. |
| 5,620,479 A | 4/1997 | Diederich |
| 5,628,317 A | 5/1997 | Starkebaum et al. |
| 5,630,426 A | 5/1997 | Shmulewitz et al. |
| 5,630,837 A | 5/1997 | Crowley |
| 5,643,319 A | 7/1997 | Green et al. |
| 5,643,330 A | 7/1997 | Holsheimer et al. |
| 5,647,361 A | 7/1997 | Damadian |
| 5,647,871 A | 7/1997 | Levine et al. |
| 5,658,278 A | 8/1997 | Imran et al. |
| 5,672,173 A | 9/1997 | Gough et al. |
| 5,681,282 A | 10/1997 | Eggers et al. |
| 5,683,366 A | 11/1997 | Eggers et al. |
| 5,685,839 A | 11/1997 | Baker et al. |
| 5,687,729 A | 11/1997 | Schaetzle |
| 5,688,267 A | 11/1997 | Panescu |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,718,231 A | 2/1998 | Chen et al. |
| 5,720,286 A | 2/1998 | Blanc et al. |
| 5,720,287 A | 2/1998 | Chapelon et al. |
| 5,722,403 A | 3/1998 | McGee et al. |
| 5,725,494 A | 3/1998 | Brisken |
| 5,728,062 A | 3/1998 | Brisken |
| 5,730,706 A | 3/1998 | Garnies |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Fleischman et al. |
| 5,735,847 A | 4/1998 | Gough et al. |
| 5,738,680 A | 4/1998 | Mueller et al. |
| 5,741,249 A | 4/1998 | Moss et al. |
| 5,743,904 A | 4/1998 | Edwards |
| 5,746,737 A | 5/1998 | Saadat |
| 5,752,969 A | 5/1998 | Cunci et al. |
| 5,755,663 A | 5/1998 | Johnson et al. |
| 5,762,066 A | 6/1998 | Law et al. |
| 5,762,616 A | 6/1998 | Talish |
| 5,766,153 A | 6/1998 | Eggers et al. |
| 5,766,231 A | 6/1998 | Bettin |
| 5,776,092 A | 7/1998 | Farin et al. |
| 5,785,705 A | 7/1998 | Baker |
| 5,800,378 A | 9/1998 | Edwards et al. |
| 5,800,429 A | 9/1998 | Edwards |
| 5,800,432 A | 9/1998 | Swanson |
| 5,807,237 A | 9/1998 | Tindel |
| 5,807,391 A | 9/1998 | Cornelius et al. |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,824,021 A | 10/1998 | Rise |
| 5,840,031 A | 11/1998 | Crowley |
| 5,843,019 A | 12/1998 | Eggers et al. |
| 5,843,021 A | 12/1998 | Edwards et al. |
| 5,844,092 A | 12/1998 | Presta et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,865,801 A | 2/1999 | Houser |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,876,398 A | 3/1999 | Muller et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,902,308 A | 5/1999 | Murphy |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,972,015 A | 10/1999 | Scribner et al. |
| 5,976,105 A | 11/1999 | Casson et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,014,588 A | 1/2000 | Fitz |
| 6,016,452 A | 1/2000 | Kasevich |
| 6,016,809 A | 1/2000 | Muller et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Lesh et al. |
| 6,030,374 A | 2/2000 | McDaniel |
| 6,030,402 A | 2/2000 | Thompson et al. |
| 6,032,673 A | 3/2000 | Alden et al. |
| 6,032,674 A | 3/2000 | Eggers et al. |
| 6,033,411 A | 3/2000 | Preissman et al. |
| 6,035,238 A | 3/2000 | Ingle et al. |
| 6,045,532 A | 4/2000 | Eggers et al. |
| 6,046,187 A | 4/2000 | Berde et al. |

(56) References Cited

U.S. PATENT DOCUMENTS

| | | |
|---|---|---|
| 6,047,214 A | 4/2000 | Gyurcsik et al. |
| 6,050,995 A | 4/2000 | Durgin |
| 6,053,172 A | 4/2000 | Hovda et al. |
| 6,053,909 A | 4/2000 | Shadduck |
| 6,038,480 A | 5/2000 | Hrdlicka et al. |
| 6,063,078 A | 5/2000 | Wittkampf |
| 6,063,079 A | 5/2000 | Hovda et al. |
| 6,066,134 A | 5/2000 | Eggers et al. |
| 6,066,139 A | 5/2000 | Ryan et al. |
| 6,068,642 A | 5/2000 | Johnson et al. |
| 6,071,279 A | 6/2000 | Fleishman et al. |
| 6,073,051 A | 6/2000 | Sharkey et al. |
| 6,074,352 A | 6/2000 | Foldes et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Clamacco |
| 6,099,514 A | 8/2000 | Sharkey et al. |
| 6,099,524 A | 8/2000 | Lipson et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,112,122 A | 8/2000 | Schwardt et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,120,502 A | 9/2000 | Michelson |
| 6,122,549 A | 9/2000 | Sharkey et al. |
| 6,126,682 A | 10/2000 | Ashley et al. |
| 6,137,209 A | 10/2000 | Dahlberg et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sharkey et al. |
| 6,169,924 B1 | 1/2001 | Meloy et al. |
| 6,171,239 B1 | 1/2001 | Humphrey |
| 6,176,857 B1 | 1/2001 | Ashley |
| 6,179,824 B1 | 1/2001 | Eggers et al. |
| 6,179,836 B1 | 1/2001 | Eggers et al. |
| 6,179,858 B1 | 1/2001 | Squire et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Elsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,216,704 B1 | 4/2001 | Ingle et al. |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,516 B1 | 5/2001 | Keilman et al. |
| 6,231,528 B1 | 5/2001 | Kaufman et al. |
| 6,231,571 B1 | 5/2001 | Ellman et al. |
| 6,231,615 B1 | 5/2001 | Preissman |
| 6,233,488 B1 | 5/2001 | Hess |
| 6,235,020 B1 | 5/2001 | Cheng et al. |
| 6,235,022 B1 | 5/2001 | Hallock et al. |
| 6,235,024 B1 | 5/2001 | Tu |
| 6,237,604 B1 | 5/2001 | Burnside et al. |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,241,734 B1 | 6/2001 | Scribner et al. |
| 6,245,064 B1 | 6/2001 | Lesh |
| 6,246,912 B1 | 6/2001 | Sluijter et al. |
| 6,248,110 B1 | 6/2001 | Reiley et al. |
| 6,248,345 B1 | 6/2001 | Goldenheim et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,270,498 B1 | 8/2001 | Michelson |
| 6,277,112 B1 | 8/2001 | Underwood et al. |
| 6,277,122 B1 | 8/2001 | McGahan et al. |
| 6,280,441 B1 | 8/2001 | Ryan |
| 6,280,456 B1 | 8/2001 | Scribner et al. |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,292,699 B1 | 9/2001 | Simon et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,425 B1 | 11/2001 | Simpson et al. |
| 6,312,426 B1 | 11/2001 | Goldberg et al. |
| 6,319,241 B1 | 11/2001 | King et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,361,531 B1 | 3/2002 | Hissong |
| 6,363,937 B1 | 4/2002 | Hovda et al. |
| 6,368,292 B1 | 4/2002 | Ogden et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,396,782 B1 | 5/2002 | Kabutz et al. |
| 6,398,782 B1 | 6/2002 | Pecor et al. |
| 6,416,507 B1 | 7/2002 | Eggers et al. |
| 6,416,508 B1 | 7/2002 | Eggers et al. |
| 6,423,057 B1 | 7/2002 | He et al. |
| 6,423,059 B1 | 7/2002 | Hanson et al. |
| 6,425,887 B1 | 7/2002 | McGuckin et al. |
| 6,426,339 B1 | 7/2002 | Berde et al. |
| 6,428,491 B1 | 8/2002 | Weiss |
| 6,432,103 B1 | 8/2002 | Ellsberry et al. |
| 6,436,060 B1 | 8/2002 | Talish |
| 6,436,098 B1 | 8/2002 | Michelson |
| 6,440,138 B1 | 8/2002 | Reiley et al. |
| 6,447,448 B1 | 9/2002 | Ishikawa et al. |
| 6,451,013 B1 | 9/2002 | Bays et al. |
| 6,454,727 B1 | 9/2002 | Bubank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,470,220 B1 | 10/2002 | Kraus et al. |
| 6,478,793 B1 | 11/2002 | Cosman et al. |
| 6,482,201 B1 | 11/2002 | Olsen et al. |
| 6,485,271 B1 | 11/2002 | Tack |
| 6,487,446 B1 | 11/2002 | Hill et al. |
| 6,491,893 B1 | 12/2002 | Babich |
| 6,493,592 B1 | 12/2002 | Leonard et al. |

(56) References Cited

U.S. PATENT DOCUMENTS

| | | |
|---|---|---|
| 6,494,902 B2 | 12/2002 | Hoey et al. |
| 6,500,173 B2 | 12/2002 | Underwood et al. |
| 6,505,075 B1 | 1/2003 | Weiner |
| 6,508,839 B1 | 1/2003 | Lambrecht et al. |
| 6,524,261 B2 | 2/2003 | Talish et al. |
| 6,527,759 B1 | 3/2003 | Tachibana et al. |
| 6,537,306 B1 | 3/2003 | Burdette et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,558,390 B2 | 5/2003 | Cragg |
| 6,560,486 B1 | 5/2003 | Osorio et al. |
| 6,562,033 B2 | 5/2003 | Shah et al. |
| 6,575,919 B1 | 6/2003 | Reiley et al. |
| 6,575,968 B1 | 6/2003 | Eggers et al. |
| 6,575,969 B1 | 6/2003 | Rittman et al. |
| 6,575,979 B1 | 6/2003 | Cragg |
| 6,578,579 B2 | 6/2003 | Burnside et al. |
| 6,582,423 B1 | 6/2003 | Thapliyal et al. |
| 6,585,656 B2 | 7/2003 | Masters |
| 6,589,237 B2 | 7/2003 | Woloszko et al. |
| 6,592,559 B1 | 7/2003 | Pakter et al. |
| 6,595,990 B1 | 7/2003 | Weinstein et al. |
| 6,599,288 B2 | 7/2003 | Maguire et al. |
| 6,602,248 B1 | 8/2003 | Sharps et al. |
| 6,604,003 B2 | 8/2003 | Fredricks et al. |
| 6,607,502 B1 | 8/2003 | Maguire et al. |
| 6,607,529 B1 | 8/2003 | Jones et al. |
| 6,608,502 B2 | 8/2003 | Aoki et al. |
| 6,622,731 B2 | 9/2003 | Daniel et al. |
| 6,623,505 B2 | 9/2003 | Scribner et al. |
| 6,632,193 B1 | 10/2003 | Davison et al. |
| 6,632,220 B1 | 10/2003 | Eggers et al. |
| 6,645,202 B1 | 11/2003 | Pless et al. |
| 6,648,883 B2 | 11/2003 | Francischelli et al. |
| 6,651,669 B1 | 11/2003 | Burnside |
| 6,659,106 B1 | 12/2003 | Hovda et al. |
| 6,663,627 B2 | 12/2003 | Francischelli et al. |
| 6,663,647 B2 | 12/2003 | Reiley et al. |
| 6,673,063 B2 | 1/2004 | Brett |
| 6,689,086 B1 | 2/2004 | Nita et al. |
| 6,689,125 B1 | 2/2004 | Keith et al. |
| 6,692,450 B1 | 2/2004 | Coleman |
| 6,699,240 B2 | 3/2004 | Francischelli |
| 6,699,242 B2 | 3/2004 | Heggeness |
| 6,709,432 B2 | 3/2004 | Ferek-Patric |
| 6,718,208 B2 | 4/2004 | Hill et al. |
| 6,719,761 B1 | 4/2004 | Relley et al. |
| 6,723,087 B2 | 4/2004 | O'Neill et al. |
| 6,723,094 B1 | 4/2004 | Desinger |
| 6,726,684 B1 | 4/2004 | Woloszko et al. |
| 6,736,810 B2 | 5/2004 | Hoey et al. |
| 6,736,835 B2 | 5/2004 | Pellegrino et al. |
| 6,745,079 B2 | 6/2004 | King |
| 6,746,447 B2 | 6/2004 | Davison et al. |
| 6,746,451 B2 | 6/2004 | Middleton et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,795,737 B2 | 9/2004 | Gielen et al. |
| 6,805,697 B1 | 10/2004 | Helm et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Clarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Elck et al. |
| 6,960,204 B2 | 11/2005 | Eggers et al. |
| 6,962,589 B2 | 11/2005 | Muller et al. |
| 6,974,453 B2 | 12/2005 | Woloszko et al. |
| 6,980,849 B2 | 12/2005 | Sasso |
| 6,981,981 B2 | 1/2006 | Reiley et al. |
| 6,989,010 B2 | 1/2006 | Francischelli et al. |
| 6,997,941 B2 | 2/2006 | Sharkey et al. |
| 7,001,383 B2 | 2/2006 | Keidar |
| 7,041,096 B2 | 5/2006 | Malis et al. |
| 7,044,954 B2 | 5/2006 | Reiley et al. |
| 7,048,743 B2 | 5/2006 | Miller et al. |
| 7,065,408 B2 | 6/2006 | Herman et al. |
| 7,081,122 B1 | 7/2006 | Relley et al. |
| 7,090,672 B2 | 8/2006 | Underwood et al. |
| 7,094,215 B2 | 8/2006 | Davison et al. |
| 7,104,989 B2 | 9/2006 | Skarda |
| 7,118,574 B2 | 10/2006 | Patel et al. |
| 7,131,969 B1 | 11/2006 | Hovda et al. |
| 7,153,307 B2 | 12/2006 | Scribner et al. |
| 7,163,536 B2 | 1/2007 | Godara |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,238,184 B2 | 7/2007 | Megerman et al. |
| 7,241,297 B2 | 7/2007 | Shaollan et al. |
| 7,250,048 B2 | 7/2007 | Francischelli et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,306,598 B2 | 12/2007 | Truckal et al. |
| 7,318,823 B2 | 1/2008 | Sharps et al. |
| 7,318,826 B2 | 1/2008 | Teitelbaum et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,399,306 B2 | 7/2008 | Relley et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,503,921 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,553,309 B2 | 6/2009 | Buysse et al. |
| 7,555,343 B2 | 6/2009 | Bleich |
| 7,559,932 B2 | 7/2009 | Truckal et al. |
| 7,569,626 B2 | 8/2009 | Truckal |
| 7,574,257 B2 | 8/2009 | Rittman |
| 7,585,300 B2 | 9/2009 | Cha |
| 7,593,778 B2 | 9/2009 | Chandran et al. |
| 7,594,913 B2 | 9/2009 | Ormsby et al. |
| 7,604,636 B1 | 10/2009 | Walters et al. |
| 7,621,952 B2 | 11/2009 | Truckal et al. |

(56) References Cited

U.S. PATENT DOCUMENTS

| | | | |
|---|---|---|---|
| 7,645,277 | B2 | 1/2010 | McClurken et al. |
| 7,678,111 | B2 | 3/2010 | Muller et al. |
| 7,678,116 | B2 | 3/2010 | Truckal et al. |
| 7,682,378 | B2 | 3/2010 | Truckai et al. |
| 7,708,733 | B2 | 5/2010 | Sanders et al. |
| 7,722,620 | B2 | 5/2010 | Truckal et al. |
| 7,731,720 | B2 | 6/2010 | Truckal et al. |
| 7,738,968 | B2 | 6/2010 | Bleich |
| 7,740,631 | B2 | 6/2010 | Bleich et al. |
| 7,749,218 | B2 | 7/2010 | Pellegrino et al. |
| 7,749,220 | B2 | 7/2010 | Schmaltz et al. |
| 7,780,733 | B2 | 8/2010 | Carver et al. |
| 7,792,588 | B2 | 9/2010 | Harding |
| 7,799,021 | B2 | 9/2010 | Leung et al. |
| 7,819,826 | B2 | 10/2010 | Diederich et al. |
| 7,819,869 | B2 | 10/2010 | Godara et al. |
| 7,824,398 | B2 | 11/2010 | Woloszko et al. |
| 7,824,404 | B2 | 11/2010 | Godara et al. |
| 7,828,804 | B2 | 11/2010 | Li et al. |
| 7,846,156 | B2 | 12/2010 | Malis et al. |
| 7,850,685 | B2 | 12/2010 | Kunis et al. |
| 7,853,326 | B2 | 12/2010 | Rittman, III |
| 7,857,813 | B2 | 12/2010 | Schmitz et al. |
| 7,879,032 | B1 | 2/2011 | Garito et al. |
| 7,887,543 | B2 | 2/2011 | Sand et al. |
| 7,892,235 | B2 | 2/2011 | Ellis |
| 7,896,870 | B2 | 3/2011 | Arless et al. |
| 7,896,909 | B2 | 3/2011 | Sharkey et al. |
| 7,901,403 | B2 | 3/2011 | Woloszko et al. |
| 7,909,827 | B2 | 3/2011 | Relley et al. |
| 7,909,873 | B2 | 3/2011 | Tan-Melecki et al. |
| 7,914,526 | B2 | 3/2011 | Lehmann et al. |
| 7,914,535 | B2 | 3/2011 | Assell et al. |
| 7,917,222 | B1 | 3/2011 | Osorio et al. |
| 7,918,849 | B2 | 4/2011 | Bleich et al. |
| 7,918,874 | B2 | 4/2011 | Siegal |
| 7,938,835 | B2 | 5/2011 | Boucher et al. |
| 7,945,331 | B2 | 5/2011 | Villms |
| 7,951,140 | B2 | 5/2011 | Arless et al. |
| 7,959,634 | B2 | 6/2011 | Sennett |
| 7,963,915 | B2 | 6/2011 | Bleich |
| 7,967,827 | B2 | 6/2011 | Osorio et al. |
| 7,972,340 | B2 | 7/2011 | Sand et al. |
| 8,000,785 | B2 | 8/2011 | Ritmann, III |
| 8,021,401 | B2 | 9/2011 | Carl et al. |
| 8,025,688 | B2 | 9/2011 | Diederich et al. |
| 8,034,052 | B2 | 10/2011 | Podhajsky |
| 8,034,071 | B2 | 10/2011 | Scribner et al. |
| 8,043,083 | B2 | 10/2011 | Nishimura et al. |
| 8,043,287 | B2 | 10/2011 | Conquergood et al. |
| 8,048,030 | B2 | 11/2011 | Conquergood et al. |
| 8,048,071 | B2 | 11/2011 | Youssef et al. |
| 8,048,083 | B2 | 11/2011 | Shadduck et al. |
| 8,052,661 | B2 | 11/2011 | McGuckin, Jr. et al. |
| 8,062,290 | B2 | 11/2011 | Buysse et al. |
| 8,066,702 | B2 | 11/2011 | Rittman, III et al. |
| 8,066,712 | B2 | 11/2011 | Truckai et al. |
| 8,070,753 | B2 | 12/2011 | Truckai et al. |
| 8,082,043 | B2 | 12/2011 | Sharkey et al. |
| 8,083,736 | B2 | 12/2011 | McClurken et al. |
| 8,096,957 | B2 | 1/2012 | Conquergood et al. |
| 8,100,896 | B2 | 1/2012 | Podhajsky |
| 8,109,933 | B2 | 2/2012 | Truckal et al. |
| 8,123,750 | B2 | 2/2012 | Norton et al. |
| 8,123,756 | B2 | 2/2012 | Miller et al. |
| 8,128,619 | B2 | 3/2012 | Sharkey et al. |
| 8,128,633 | B2 | 3/2012 | Linderman et al. |
| 8,162,933 | B2 | 4/2012 | Francischelli et al. |
| 8,163,031 | B2 | 4/2012 | Truckal et al. |
| 8,172,846 | B2 | 5/2012 | Brunnett et al. |
| 8,182,477 | B2 | 5/2012 | Orszulak et al. |
| 8,187,312 | B2 | 5/2012 | Sharkey et al. |
| 8,192,424 | B2 | 6/2012 | Woloszko et al. |
| 8,192,435 | B2 | 6/2012 | Bleich et al. |
| 8,216,223 | B2 | 7/2012 | Wham et al. |
| 8,226,697 | B2 | 7/2012 | Sharkey et al. |
| 8,231,616 | B2 | 7/2012 | McPherson et al. |
| 8,241,335 | B2 | 8/2012 | Truckai et al. |
| 8,246,627 | B2 | 8/2012 | Vanleeuwen et al. |
| 8,265,747 | B2 | 9/2012 | Rittman, III et al. |
| 8,282,628 | B2 | 10/2012 | Paul et al. |
| 8,292,882 | B2 | 10/2012 | Danek et al. |
| 8,292,887 | B2 | 10/2012 | Woloszko et al. |
| 8,323,277 | B2 | 12/2012 | Vilims |
| 8,323,279 | B2 | 12/2012 | Dahla et al. |
| 8,343,146 | B2 | 1/2013 | Godara |
| 8,348,946 | B2 | 1/2013 | McClurken et al. |
| 8,348,955 | B2 | 1/2013 | Truckal et al. |
| 8,355,799 | B2 | 1/2013 | Marion et al. |
| 8,361,063 | B2 | 1/2013 | Godara |
| 8,361,067 | B2 | 1/2013 | Pellegrino et al. |
| 8,406,886 | B2 | 3/2013 | Gaunt |
| 8,409,289 | B2 | 4/2013 | Truckal et al. |
| 8,414,509 | B2 | 4/2013 | Diederich et al. |
| 8,414,571 | B2 | 4/2013 | Pellegrino et al. |
| 8,419,730 | B2 | 4/2013 | Pellegrino et al. |
| 8,419,731 | B2 | 4/2013 | Pellegrino et al. |
| 8,425,507 | B2 | 4/2013 | Pellegrino et al. |
| 8,430,887 | B2 | 4/2013 | Truckai et al. |
| 8,444,636 | B2 | 5/2013 | Shadduck et al. |
| 8,444,640 | B2 | 5/2013 | Demarais et al. |
| 8,454,594 | B2 | 6/2013 | Demarais et al. |
| 8,460,382 | B2 | 6/2013 | Helm et al. |
| 8,475,449 | B2 | 7/2013 | Werneth et al. |
| 8,486,063 | B2 | 7/2013 | Werneth et al. |
| 8,487,021 | B2 | 7/2013 | Truckai et al. |
| 8,504,147 | B2 | 8/2013 | Deem et al. |
| 8,505,545 | B2 | 8/2013 | Conquergood et al. |
| 8,518,036 | B2 | 8/2013 | Leung et al. |
| 8,523,871 | B2 | 9/2013 | Truckai et al. |
| 8,535,309 | B2 | 9/2013 | Pellegrino et al. |
| 8,540,723 | B2 | 9/2013 | Shadduck |
| 8,556,910 | B2 | 10/2013 | Truckal et al. |
| 8,556,911 | B2 | 10/2013 | Mehta et al. |
| 8,560,062 | B2 | 10/2013 | Rittman, III et al. |
| 8,562,598 | B2 | 10/2013 | Falkenstein et al. |
| 8,562,607 | B2 | 10/2013 | Truckal et al. |
| 8,562,620 | B2 | 10/2013 | Truckai et al. |
| 8,579,903 | B2 | 11/2013 | Carl |
| 8,585,694 | B2 | 11/2013 | Amoah et al. |
| 8,591,507 | B2 | 11/2013 | Kramer et al. |
| 8,597,301 | B2 | 12/2013 | Mitchell |
| 8,603,088 | B2 | 12/2013 | Stern et al. |
| 8,613,744 | B2 | 12/2013 | Pellegrino et al. |
| 8,617,156 | B2 | 12/2013 | Werneth et al. |
| 8,623,014 | B2 | 1/2014 | Pellegrino et al. |
| 8,623,025 | B2 | 1/2014 | Tan-Malecki et al. |
| 8,628,528 | B2 | 1/2014 | Pellegrino et al. |
| 8,636,736 | B2 | 1/2014 | Yates et al. |
| 8,644,941 | B2 | 2/2014 | Rooney et al. |
| 8,657,814 | B2 | 2/2014 | Werneth et al. |
| 8,663,266 | B1 | 3/2014 | Obsuth |
| 8,672,934 | B2 | 3/2014 | Benamou et al. |
| 8,676,309 | B2 | 3/2014 | Deem et al. |
| 8,679,023 | B2 | 3/2014 | Kobayashi et al. |
| 8,690,884 | B2 | 4/2014 | Linderman et al. |
| 8,696,679 | B2 | 4/2014 | Shadduck et al. |
| RE44,883 | E | 5/2014 | Cha |
| 8,740,897 | B2 | 6/2014 | Leung et al. |
| 8,747,359 | B2 | 6/2014 | Pakter et al. |
| 8,747,398 | B2 | 6/2014 | Behnke |
| 8,758,349 | B2 | 6/2014 | Germain et al. |
| 8,764,761 | B2 | 7/2014 | Truckal et al. |
| 8,771,265 | B2 | 7/2014 | Truckai |
| 8,771,276 | B2 | 7/2014 | Linderman |
| 8,774,913 | B2 | 7/2014 | Demarais et al. |
| 8,774,924 | B2 | 7/2014 | Weiner |
| 8,777,479 | B2 | 7/2014 | Kwan et al. |
| 8,784,411 | B2 | 7/2014 | Leuthardt et al. |
| 8,795,270 | B2 | 8/2014 | Drake |
| 8,808,161 | B2 | 8/2014 | Gregg et al. |
| 8,808,284 | B2 | 8/2014 | Pellegrino et al. |
| 8,814,873 | B2 | 8/2014 | Schaller et al. |
| 8,818,503 | B2 | 8/2014 | Rittman, III |

(56) References Cited

U.S. PATENT DOCUMENTS

| | | |
|---|---|---|
| 8,821,488 B2 | 9/2014 | Stewart et al. |
| 8,845,631 B2 | 9/2014 | Werneth et al. |
| 8,864,759 B2 | 10/2014 | Godara et al. |
| 8,864,760 B2 | 10/2014 | Kramer et al. |
| 8,864,777 B2 | 10/2014 | Harrison et al. |
| 8,882,755 B2 | 11/2014 | Leung et al. |
| 8,882,759 B2 | 11/2014 | Manley et al. |
| 8,882,764 B2 | 11/2014 | Pellegrino et al. |
| 8,894,658 B2 | 11/2014 | Linderman et al. |
| 8,911,497 B2 | 12/2014 | Chavatte et al. |
| 8,915,949 B2 | 12/2014 | Diederich et al. |
| 8,926,620 B2 | 1/2015 | Chasmawala et al. |
| 8,932,300 B2 | 1/2015 | Shadduck et al. |
| 8,939,969 B2 | 1/2015 | Temelli et al. |
| 8,968,288 B2 | 3/2015 | Brannan |
| 8,989,859 B2 | 3/2015 | Deem et al. |
| 8,992,522 B2 | 3/2015 | Pellegrino et al. |
| 8,992,523 B2 | 3/2015 | Pellegrino et al. |
| 9,005,210 B2 | 4/2015 | Truckai et al. |
| 9,008,793 B1 | 4/2015 | Cosman, Sr. et al. |
| 9,017,325 B2 | 4/2015 | Pellegrino et al. |
| 9,023,038 B2 | 5/2015 | Pellegrino et al. |
| 9,028,488 B2 | 5/2015 | Goshayeshgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,066,769 B2 | 6/2015 | Truckai et al. |
| 9,078,761 B2 | 7/2015 | Godara et al. |
| 9,095,359 B2 | 8/2015 | Robert et al. |
| 9,113,896 B2 | 8/2015 | Muller et al. |
| 9,113,911 B2 | 8/2015 | Sherman |
| 9,113,925 B2 | 8/2015 | Smith et al. |
| 9,113,950 B2 | 8/2015 | Schultz et al. |
| 9,113,974 B2 | 8/2015 | Germain |
| 9,119,639 B2 | 9/2015 | Kuntz |
| 9,119,647 B2 | 9/2015 | Brannan |
| 9,119,650 B2 | 9/2015 | Brannan et al. |
| 9,125,671 B2 | 9/2015 | Germain et al. |
| 9,131,597 B2 | 9/2015 | Taft et al. |
| 9,149,652 B2 | 10/2015 | Wenz et al. |
| 9,151,680 B2 | 10/2015 | Brannan |
| 9,155,895 B2 | 10/2015 | Wacnik et al. |
| 9,161,735 B2 | 10/2015 | Bradford et al. |
| 9,161,797 B2 | 10/2015 | Truckai et al. |
| 9,161,798 B2 | 10/2015 | Truckai et al. |
| 9,161,805 B2 | 10/2015 | Isenberg |
| 9,161,809 B2 | 10/2015 | Germain et al. |
| 9,161,814 B2 | 10/2015 | Brannan et al. |
| 9,168,054 B2 | 10/2015 | Turner et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,179,972 B2 | 11/2015 | Olson |
| 9,180,416 B2 | 11/2015 | Phan et al. |
| 9,186,197 B2 | 11/2015 | McKay |
| 9,192,308 B2 | 11/2015 | Brannan et al. |
| 9,192,397 B2 | 11/2015 | Sennett et al. |
| 9,198,684 B2 | 12/2015 | Arthur et al. |
| 9,216,053 B2 | 12/2015 | Godara et al. |
| 9,226,756 B2 | 1/2016 | Teisen et al. |
| 9,232,954 B2 | 1/2016 | Steiner et al. |
| 9,237,916 B2 | 1/2016 | Crainich et al. |
| 9,238,139 B2 | 1/2016 | Degiorgio et al. |
| 9,241,057 B2 | 1/2016 | Van Wyk et al. |
| 9,241,729 B2 | 1/2016 | Juntz et al. |
| 9,241,760 B2 | 1/2016 | Godara et al. |
| 9,247,970 B2 | 2/2016 | Telsen |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,979 B2 | 3/2016 | O'Neil et al. |
| 9,282,988 B2 | 3/2016 | Goshayeshgar |
| 9,283,015 B2 | 3/2016 | Tan-Malecki et al. |
| 9,289,607 B2 | 3/2016 | Su et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashlach |
| 9,314,618 B2 | 4/2016 | Imran et al. |
| 9,333,033 B2 | 5/2016 | Gliner |
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |
| 9,345,537 B2 | 5/2016 | Harrison et al. |
| 9,345,538 B2 | 5/2016 | Deem et al. |
| 9,351,739 B2 | 5/2016 | Mahoney et al. |
| 9,358,059 B2 | 6/2016 | Linderman et al. |
| 9,358,067 B2 | 6/2016 | Lee et al. |
| 9,358,396 B2 | 6/2016 | Holley |
| 9,364,242 B2 | 6/2016 | Tornier et al. |
| 9,364,286 B2 | 6/2016 | Werneth et al. |
| 9,370,348 B2 | 6/2016 | Tally et al. |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Robert et al. |
| 9,375,279 B2 | 6/2016 | Brannan |
| 9,375,283 B2 | 6/2016 | Arts et al. |
| 9,381,024 B2 | 7/2016 | Globerman et al. |
| 9,381,045 B2 | 7/2016 | Donner et al. |
| 9,381,050 B2 | 7/2016 | Lee et al. |
| 9,381,359 B2 | 7/2016 | Parramon et al. |
| 9,387,094 B2 | 7/2016 | Manrique et al. |
| 9,393,416 B2 | 7/2016 | Rooney et al. |
| 9,398,931 B2 | 7/2016 | Wittenberger et al. |
| 9,399,144 B2 | 7/2016 | Howard |
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,439,693 B2 | 9/2016 | Childs et al. |
| 9,439,721 B2 | 9/2016 | Werneth et al. |
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,565 B2 | 10/2016 | Shikhman et al. |
| 9,474,906 B2 | 10/2016 | Sachs et al. |
| 9,480,485 B2 | 11/2016 | Aho et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |

(56) References Cited

U.S. PATENT DOCUMENTS

| | | |
|---|---|---|
| 9,492,664 B2 | 11/2016 | Peterson |
| 9,504,372 B2 | 11/2016 | Kim |
| 9,504,481 B2 | 11/2016 | Germain et al. |
| 9,504,506 B2 | 11/2016 | Crainich et al. |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,513,761 B2 | 12/2016 | Shikhman et al. |
| 9,517,077 B2 | 12/2016 | Blain et al. |
| 9,517,200 B2 | 12/2016 | Bleier |
| 9,526,507 B2 | 12/2016 | Germain |
| 9,526,551 B2 | 12/2016 | Linderman |
| 9,526,559 B2 | 12/2016 | Benamou et al. |
| 9,532,828 B2 | 1/2017 | Condie et al. |
| 9,549,772 B2 | 1/2017 | Carl |
| 9,550,041 B2 | 1/2017 | Bedell |
| 9,555,037 B2 | 1/2017 | Podhajsky |
| 9,556,101 B2 | 1/2017 | Robertson et al. |
| 9,556,449 B2 | 1/2017 | Basu et al. |
| 9,566,449 B2 | 2/2017 | Perryman et al. |
| 9,572,976 B2 | 2/2017 | Howard et al. |
| 9,572,986 B2 | 2/2017 | Moffitt |
| 9,579,127 B2 | 2/2017 | Kostuik et al. |
| 9,579,518 B2 | 2/2017 | Gertner |
| 9,597,091 B2 | 3/2017 | Bromer |
| 9,597,148 B2 | 3/2017 | Olson |
| RE46,356 E | 4/2017 | Pellegrino et al. |
| 9,610,083 B2 | 4/2017 | Kuntz |
| 9,610,117 B2 | 4/2017 | Germain |
| 9,636,175 B2 | 5/2017 | Stern et al. |
| 9,642,629 B2 | 5/2017 | Griffiths et al. |
| 9,649,116 B2 | 5/2017 | Germain |
| 9,681,889 B1 | 6/2017 | Greenhalgh et al. |
| 9,687,255 B2 | 6/2017 | Sennett et al. |
| 9,724,107 B2 | 8/2017 | Pellegrino et al. |
| 9,724,151 B2 * | 8/2017 | Edidin .................. A61B 18/04 |
| 9,730,707 B2 | 8/2017 | Sasaki et al. |
| 9,743,854 B2 | 8/2017 | Stewart et al. |
| 9,743,938 B2 | 8/2017 | Germain et al. |
| 9,750,560 B2 | 9/2017 | Ballakur et al. |
| 9,757,193 B2 | 9/2017 | Zarins et al. |
| 9,770,280 B2 | 9/2017 | Diederich et al. |
| 9,775,627 B2 | 10/2017 | Patel et al. |
| 9,782,221 B2 | 10/2017 | Srinivasan |
| 9,795,802 B2 | 10/2017 | Mohamed et al. |
| 9,814,514 B2 | 11/2017 | Shelton, IV et al. |
| 9,844,406 B2 | 12/2017 | Edwards et al. |
| 9,848,944 B2 | 12/2017 | Sutton et al. |
| 9,872,687 B2 | 1/2018 | Tornier et al. |
| 9,872,691 B2 | 1/2018 | Griffiths et al. |
| 9,877,707 B2 | 1/2018 | Godara et al. |
| 9,913,675 B2 | 3/2018 | Germain |
| 10,028,753 B2 | 7/2018 | Pellegrino et al. |
| 10,028,784 B2 | 7/2018 | Kramer et al. |
| 10,052,152 B2 | 8/2018 | Tegg et al. |
| 10,111,674 B2 | 10/2018 | Crainich et al. |
| 10,111,704 B2 | 10/2018 | Pellegrino et al. |
| 10,123,809 B2 | 11/2018 | Germain |
| 10,245,092 B2 | 4/2019 | Germain |
| 10,265,099 B2 | 4/2019 | Pellegrino et al. |
| 10,272,271 B2 | 4/2019 | Diederich et al. |
| 10,292,716 B2 | 5/2019 | Aho et al. |
| 10,292,719 B2 | 5/2019 | Burger et al. |
| 10,299,805 B2 | 5/2019 | Germain et al. |
| 10,327,841 B2 | 6/2019 | Germain |
| 10,357,258 B2 | 7/2019 | Patel et al. |
| 10,383,641 B2 | 8/2019 | LeRoy et al. |
| 10,390,877 B2 | 8/2019 | Heggeness et al. |
| 10,441,295 B2 | 10/2019 | Brockman et al. |
| 10,448,995 B2 | 10/2019 | Olson |
| 10,456,187 B2 * | 10/2019 | Edidin .................. A61B 18/04 |
| 10,463,380 B2 | 11/2019 | Purdy et al. |
| 10,463,423 B2 | 11/2019 | Sutton et al. |
| 10,470,781 B2 | 11/2019 | Purdy et al. |
| 10,478,241 B2 | 11/2019 | Purdy et al. |
| 10,478,246 B2 | 11/2019 | Pellegrino et al. |
| 10,493,247 B2 | 12/2019 | Goshayeshgar |
| 10,499,960 B2 | 12/2019 | Sinnott et al. |
| 10,517,611 B2 | 12/2019 | Patel et al. |
| 10,524,805 B2 | 1/2020 | Zilberman et al. |
| 10,588,691 B2 | 3/2020 | Pellegrino et al. |
| 10,589,131 B2 | 3/2020 | Diederich et al. |
| 10,603,522 B2 | 3/2020 | Diederich et al. |
| 10,624,652 B2 | 4/2020 | Germain et al. |
| 10,660,656 B2 | 5/2020 | Purdy et al. |
| 10,898,254 B2 | 1/2021 | Diederich et al. |
| 10,905,440 B2 | 2/2021 | Pellegrino et al. |
| RE48,460 E | 3/2021 | Pellegrino et al. |
| 11,007,010 B2 | 5/2021 | Donovan et al. |
| 11,026,734 B2 | 6/2021 | Truckai et al. |
| 11,026,744 B2 | 6/2021 | Purdy et al. |
| 11,052,267 B2 | 7/2021 | Diederich et al. |
| 11,065,046 B2 * | 7/2021 | Edidin .................. A61B 18/04 |
| 11,123,103 B2 | 9/2021 | Donovan et al. |
| 11,160,563 B2 | 11/2021 | Patel et al. |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0027295 A1 | 10/2001 | Dulak et al. |
| 2001/0029370 A1 | 10/2001 | Hovda et al. |
| 2001/0029373 A1 | 10/2001 | Baker et al. |
| 2001/0029393 A1 | 10/2001 | Tierney et al. |
| 2001/0032001 A1 | 10/2001 | Ricart et al. |
| 2001/0047167 A1 * | 11/2001 | Heggeness .......... A61B 18/148 606/41 |
| 2001/0049522 A1 | 12/2001 | Eggers et al. |
| 2001/0049527 A1 | 12/2001 | Cragg |
| 2001/0051802 A1 | 12/2001 | Woloszko et al. |
| 2001/0053885 A1 | 12/2001 | Gielen et al. |
| 2001/0056280 A1 | 12/2001 | Underwood et al. |
| 2002/0016583 A1 | 2/2002 | Cragg |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0049438 A1 | 4/2002 | Sharkey et al. |
| 2002/0095144 A1 | 4/2002 | Carl |
| 2002/0052600 A1 | 5/2002 | Davison et al. |
| 2002/0068930 A1 | 6/2002 | Tasto et al. |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0111661 A1 | 8/2002 | Cross et al. |
| 2002/0115945 A1 | 8/2002 | D'Luzansky et al. |
| 2002/0120259 A1 | 8/2002 | Lettice et al. |
| 2002/0133148 A1 | 9/2002 | Daniel et al. |
| 2002/0147444 A1 | 10/2002 | Shah et al. |
| 2002/0151885 A1 | 10/2002 | Underwood et al. |
| 2002/0165532 A1 | 11/2002 | Hill et al. |
| 2002/0183758 A1 | 12/2002 | Middleton et al. |
| 2002/0188284 A1 | 12/2002 | To et al. |
| 2002/0188290 A1 | 12/2002 | Sharkey et al. |
| 2002/0193708 A1 | 12/2002 | Horzewski et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0014088 A1 | 1/2003 | Fang et al. |
| 2003/0028147 A1 | 2/2003 | Aves et al. |
| 2003/0028189 A1 | 2/2003 | Woloszko et al. |
| 2003/0040742 A1 | 2/2003 | Underwood et al. |
| 2003/0055418 A1 | 3/2003 | Tasto et al. |
| 2003/0069569 A1 | 4/2003 | Burdette et al. |
| 2003/0083592 A1 | 5/2003 | Faciszewski |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0139652 A1 | 7/2003 | Kang et al. |
| 2003/0158545 A1 | 8/2003 | Hovda et al. |
| 2003/0181963 A1 | 9/2003 | Pellegrino et al. |

(56) References Cited

U.S. PATENT DOCUMENTS

| | | |
|---|---|---|
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2003/0225331 A1 | 12/2003 | Diederich et al. |
| 2003/0225364 A1 | 12/2003 | Kraft |
| 2004/0006339 A1 | 1/2004 | Underwood et al. |
| 2004/0015163 A1 | 1/2004 | Buysse et al. |
| 2004/0024399 A1 | 2/2004 | Sharps et al. |
| 2004/0054366 A1 | 3/2004 | Davison et al. |
| 2004/0064023 A1 | 4/2004 | Thomas et al. |
| 2004/0064136 A1 | 4/2004 | Crombie et al. |
| 2004/0064137 A1* | 4/2004 | Pellegrino .......... A61B 18/1477 606/41 |
| 2004/0068242 A1 | 4/2004 | McGuckin, Jr. |
| 2004/0082942 A1 | 4/2004 | Katzman |
| 2004/0082946 A1 | 4/2004 | Malis et al. |
| 2004/0087937 A1 | 5/2004 | Eggers et al. |
| 2004/0111087 A1 | 6/2004 | Stern et al. |
| 2004/0116922 A1 | 6/2004 | Hovda et al. |
| 2004/0120668 A1 | 6/2004 | Loeb |
| 2004/0120891 A1 | 6/2004 | Hill et al. |
| 2004/0133124 A1 | 7/2004 | Bates et al. |
| 2004/0162559 A1 | 8/2004 | Arramon |
| 2004/0186544 A1 | 9/2004 | King |
| 2004/0193151 A1 | 9/2004 | To et al. |
| 2004/0220577 A1 | 11/2004 | Cragg et al. |
| 2004/0225228 A1* | 11/2004 | Ferree ................ A61B 17/1626 600/554 |
| 2004/0230190 A1 | 11/2004 | Dahla et al. |
| 2004/0267269 A1 | 12/2004 | Middleton et al. |
| 2005/0004634 A1 | 1/2005 | Ricart et al. |
| 2005/0010095 A1 | 1/2005 | Stewart et al. |
| 2005/0010203 A1 | 1/2005 | Edwards et al. |
| 2005/0010205 A1 | 1/2005 | Hovda et al. |
| 2005/0043737 A1 | 2/2005 | Reiley et al. |
| 2005/0055096 A1 | 3/2005 | Serhan et al. |
| 2005/0124989 A1 | 6/2005 | Suddaby |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0182417 A1 | 8/2005 | Pagano |
| 2005/0192564 A1 | 9/2005 | Cosman et al. |
| 2005/0209610 A1 | 9/2005 | Carrison |
| 2005/0209659 A1 | 9/2005 | Pellegrino et al. |
| 2005/0216018 A1 | 9/2005 | Sennett |
| 2005/0234445 A1 | 10/2005 | Conquergood et al. |
| 2005/0261754 A1 | 11/2005 | Woloszko |
| 2005/0267552 A1 | 12/2005 | Conquergood et al. |
| 2005/0278007 A1 | 12/2005 | Godara |
| 2005/0283148 A1 | 12/2005 | Janssen et al. |
| 2006/0004369 A1 | 1/2006 | Patel et al. |
| 2006/0036264 A1 | 2/2006 | Selover et al. |
| 2006/0052743 A1 | 3/2006 | Reynolds |
| 2006/0064101 A1 | 3/2006 | Arramon |
| 2006/0095026 A1 | 5/2006 | Ricart et al. |
| 2006/0095028 A1 | 5/2006 | Bleich |
| 2006/0106375 A1 | 5/2006 | Werneth et al. |
| 2006/0106376 A1 | 5/2006 | Godara et al. |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0200121 A1 | 9/2006 | Mowery |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0206166 A1 | 9/2006 | Weiner |
| 2006/0217736 A1 | 9/2006 | Kaneko et al. |
| 2006/0229625 A1 | 10/2006 | Truckai et al. |
| 2006/0247746 A1 | 11/2006 | Danek et al. |
| 2006/0253117 A1 | 11/2006 | Hovda et al. |
| 2006/0259026 A1 | 11/2006 | Godara et al. |
| 2006/0264957 A1 | 11/2006 | Cragg et al. |
| 2006/0264965 A1 | 11/2006 | Shadduck et al. |
| 2006/0265014 A1 | 11/2006 | Demarais et al. |
| 2006/0276749 A1 | 12/2006 | Selmon et al. |
| 2006/0287649 A1 | 12/2006 | Ormsby et al. |
| 2007/0027449 A1 | 2/2007 | Godara et al. |
| 2007/0055316 A1 | 3/2007 | Godara et al. |
| 2007/0066987 A1 | 3/2007 | Scanlan et al. |
| 2007/0074719 A1 | 4/2007 | Danek et al. |
| 2007/0118142 A1 | 5/2007 | Krueger et al. |
| 2007/0129715 A1 | 6/2007 | Eggers et al. |
| 2007/0142791 A1 | 6/2007 | Yeung et al. |
| 2007/0142842 A1 | 6/2007 | Krueger et al. |
| 2007/0149966 A1 | 6/2007 | Dahla et al. |
| 2007/0179497 A1 | 8/2007 | Eggers et al. |
| 2007/0185231 A1 | 8/2007 | Liu et al. |
| 2007/0213584 A1 | 9/2007 | Kim et al. |
| 2007/0213735 A1 | 9/2007 | Saadat et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0065062 A1 | 3/2008 | Leung et al. |
| 2008/0091207 A1 | 4/2008 | Truckal et al. |
| 2008/0114364 A1 | 5/2008 | Goldin et al. |
| 2008/0119844 A1 | 5/2008 | Woloszko et al. |
| 2008/0119845 A1* | 5/2008 | Stone .................... A61F 2/4611 606/41 |
| 2008/0119846 A1 | 5/2008 | Rioux |
| 2008/0132890 A1 | 6/2008 | Woloszko et al. |
| 2008/0144364 A1 | 6/2008 | Lee et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2008/0294167 A1 | 11/2008 | Schumacher et al. |
| 2009/0030308 A1 | 1/2009 | Bradford et al. |
| 2009/0054951 A1 | 2/2009 | Leuthardt et al. |
| 2009/0069807 A1 | 3/2009 | Eggers et al. |
| 2009/0076520 A1 | 3/2009 | Choi |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149878 A1 | 6/2009 | Truckai et al. |
| 2009/0204192 A1 | 8/2009 | Carlton et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0179556 A1 | 7/2010 | Scribner et al. |
| 2010/0185082 A1 | 7/2010 | Chandran et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0298737 A1 | 11/2010 | Koehler |
| 2010/0298832 A1 | 11/2010 | Lau et al. |
| 2010/0324506 A1 | 12/2010 | Pellegrino et al. |
| 2011/0022133 A1 | 1/2011 | Diederich et al. |
| 2011/0034884 A9* | 2/2011 | Pellegrino ............... A61F 7/007 604/272 |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0130751 A1 | 6/2011 | Malis et al. |
| 2011/0144524 A1 | 6/2011 | Fish et al. |
| 2011/0196361 A1 | 8/2011 | Vilims |

(56) References Cited

U.S. PATENT DOCUMENTS

| | | |
|---|---|---|
| 2011/0206260 A1 | 8/2011 | Bergmans et al. |
| 2011/0264098 A1 | 10/2011 | Cobbs |
| 2011/0276001 A1 | 11/2011 | Schultz et al. |
| 2011/0295261 A1 | 12/2011 | Germain |
| 2011/0319765 A1 | 12/2011 | Gertner et al. |
| 2012/0029420 A1 | 2/2012 | Vilims |
| 2012/0116266 A1 | 5/2012 | House et al. |
| 2012/0136346 A1 | 5/2012 | Condie et al. |
| 2012/0136348 A1 | 5/2012 | Condie et al. |
| 2012/0143090 A1 | 6/2012 | Hay et al. |
| 2012/0172858 A1 | 7/2012 | Harrison et al. |
| 2012/0172859 A1 | 7/2012 | Condie et al. |
| 2012/0191095 A1 | 7/2012 | Burger et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226273 A1 | 9/2012 | Nguyen et al. |
| 2012/0239050 A1 | 9/2012 | Linderman |
| 2012/0265186 A1 | 10/2012 | Burger et al. |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0060244 A1 | 3/2013 | Godara et al. |
| 2013/0079810 A1 | 3/2013 | Isenberg |
| 2013/0116688 A1 | 5/2013 | Kunis et al. |
| 2013/0197508 A1 | 8/2013 | Shikhman et al. |
| 2013/0231654 A1 | 9/2013 | Germain |
| 2013/0237979 A1 | 9/2013 | Shikhman et al. |
| 2013/0103022 A1 | 10/2013 | Sutton et al. |
| 2013/0261507 A1 | 10/2013 | Diederich et al. |
| 2013/0274784 A1 | 10/2013 | Lenker et al. |
| 2013/0296767 A1 | 11/2013 | Zarins et al. |
| 2013/0324993 A1 | 12/2013 | McCarthey et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0331840 A1 | 12/2013 | Teisen et al. |
| 2013/0345765 A1 | 12/2013 | Brockman et al. |
| 2014/0031715 A1* | 1/2014 | Sherar ............... A61B 18/148 607/101 |
| 2014/0039500 A1 | 2/2014 | Pellegrino et al. |
| 2014/0046245 A1 | 2/2014 | Cornacchia |
| 2014/0046328 A1 | 2/2014 | Schumacher et al. |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0194887 A1 | 7/2014 | Shenoy |
| 2014/0221967 A1 | 8/2014 | Childs et al. |
| 2014/0236137 A1 | 8/2014 | Tran et al. |
| 2014/0236144 A1 | 8/2014 | Krueger et al. |
| 2014/0243823 A1 | 8/2014 | Godara et al. |
| 2014/0243943 A1 | 8/2014 | Rao et al. |
| 2014/0257265 A1 | 9/2014 | Godara et al. |
| 2014/0257296 A1 | 9/2014 | Morgenstern Lopez |
| 2014/0271717 A1 | 9/2014 | Goshayeshgar et al. |
| 2014/0276728 A1 | 9/2014 | Goshayeshgar et al. |
| 2014/0276744 A1 | 9/2014 | Arthur et al. |
| 2014/0288544 A1 | 9/2014 | Diederich et al. |
| 2014/0288546 A1 | 9/2014 | Sherman et al. |
| 2014/0296850 A1 | 10/2014 | Condie et al. |
| 2014/0303610 A1 | 10/2014 | McCarthy et al. |
| 2014/0303614 A1 | 10/2014 | McCarthy et al. |
| 2014/0316405 A1 | 10/2014 | Pellegrino et al. |
| 2014/0316413 A1 | 10/2014 | Burger et al. |
| 2014/0324051 A1 | 10/2014 | Pellegrino et al. |
| 2014/0330332 A1 | 11/2014 | Danek et al. |
| 2014/0336630 A1 | 11/2014 | Woloszko et al. |
| 2014/0336667 A1 | 11/2014 | Pellegrino et al. |
| 2014/0364842 A1 | 12/2014 | Werneth et al. |
| 2014/0371740 A1 | 12/2014 | Germain et al. |
| 2015/0005614 A1 | 1/2015 | Heggeness et al. |
| 2015/0005767 A1 | 1/2015 | Werneth et al. |
| 2015/0045783 A1 | 2/2015 | Edidin |
| 2015/0057658 A1 | 2/2015 | Sutton et al. |
| 2015/0065945 A1 | 3/2015 | Zarins et al. |
| 2015/0073515 A1 | 3/2015 | Turovskly et al. |
| 2015/0105701 A1 | 4/2015 | Mayer et al. |
| 2015/0141876 A1 | 5/2015 | Diederich et al. |
| 2015/0157402 A1 | 6/2015 | Kunis et al. |
| 2015/0164546 A1 | 6/2015 | Pellegrino et al. |
| 2015/0196358 A1 | 7/2015 | Goshayeshgar |
| 2015/0216588 A1 | 8/2015 | Deem et al. |
| 2015/0231417 A1 | 8/2015 | Metcalf et al. |
| 2015/0272655 A1 | 10/2015 | Condie et al. |
| 2015/0273208 A1 | 10/2015 | Hamilton |
| 2015/0297246 A1 | 10/2015 | Patel et al. |
| 2015/0297282 A1 | 10/2015 | Cadouri |
| 2015/0320480 A1 | 11/2015 | Cosman, Jr. et al. |
| 2015/0335349 A1 | 11/2015 | Pellegrino et al. |
| 2015/0335382 A1 | 11/2015 | Pellegrino et al. |
| 2015/0342619 A1 | 12/2015 | Weitzman |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0045207 A1 | 2/2016 | Kovacs et al. |
| 2016/0045256 A1 | 2/2016 | Godara et al. |
| 2016/0051831 A1 | 2/2016 | Lundmark et al. |
| 2016/0059007 A1 | 3/2016 | Koop |
| 2016/0074068 A1 | 3/2016 | Patwardhan |
| 2016/0074133 A1 | 3/2016 | Shikhman et al. |
| 2016/0074279 A1 | 3/2016 | Shin |
| 2016/0074661 A1 | 3/2016 | Lipani |
| 2016/0081716 A1 | 3/2016 | Boling et al. |
| 2016/0081810 A1 | 3/2016 | Reiley et al. |
| 2016/0095721 A1 | 4/2016 | Schell et al. |
| 2016/0106443 A1 | 4/2016 | Kuntz et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166302 A1 | 6/2016 | Tan-Malecki et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0199117 A1 | 7/2016 | Druma |
| 2016/0213927 A1 | 7/2016 | McGee et al. |
| 2016/0220317 A1 | 8/2016 | Shikhman et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |

(56) References Cited

U.S. PATENT DOCUMENTS

| | | |
|---|---|---|
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0262904 A1 | 9/2016 | Schaller et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0278861 A1 | 9/2016 | Ko |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0302925 A1 | 10/2016 | Keogh et al. |
| 2016/0302936 A1 | 10/2016 | Billon et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 11/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375259 A1 | 12/2016 | Davis et al. |
| 2017/0000501 A1 | 1/2017 | Aho et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049500 A1 | 2/2017 | Shikhman et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0056028 A1 | 3/2017 | Germain et al. |
| 2017/0065329 A1 | 3/2017 | Benamou et al. |
| 2017/0112507 A1 | 4/2017 | Crainich et al. |
| 2017/0119461 A1 | 5/2017 | Godara et al. |
| 2017/0128080 A1 | 5/2017 | Torrie |
| 2017/0128112 A1 | 5/2017 | Germain |
| 2017/0135742 A1 | 5/2017 | Lee et al. |
| 2017/0164998 A1 | 6/2017 | Klimovitch |
| 2017/0172650 A1 | 6/2017 | Germain |
| 2017/0181788 A1 | 6/2017 | Dastjerdi et al. |
| 2017/0202613 A1 | 7/2017 | Pellegrino et al. |
| 2017/0238943 A1 | 8/2017 | Sennett et al. |
| 2017/0266419 A1 | 9/2017 | Goshayeshgar |
| 2017/0303983 A1 | 10/2017 | Linderman et al. |
| 2017/0312007 A1 | 11/2017 | Harley et al. |
| 2017/0333052 A1 | 11/2017 | Ding et al. |
| 2018/0021048 A1 | 1/2018 | Pellegrino et al. |
| 2018/0042656 A1 | 2/2018 | Edidin |
| 2018/0055539 A1 | 3/2018 | Pellegrino |
| 2018/0103964 A1 | 4/2018 | Patel et al. |
| 2018/0153604 A1 | 6/2018 | Ayvazyan et al. |
| 2018/0161047 A1 | 6/2018 | Purdy et al. |
| 2018/0193088 A1 | 7/2018 | Sutton et al. |
| 2019/0029698 A1 | 1/2019 | Pellegrino et al. |
| 2019/0038296 A1 | 2/2019 | Pellegrino |
| 2019/0038343 A1 | 2/2019 | Sutton et al. |
| 2019/0038344 A1 | 2/2019 | Pellegrino |
| 2019/0038345 A1 | 2/2019 | Pellegrino |
| 2019/0090933 A1 | 3/2019 | Pellegrino et al. |
| 2019/0110833 A1 | 4/2019 | Pellegrino et al. |
| 2019/0118003 A1 | 4/2019 | Diederich et al. |
| 2019/0118004 A1 | 4/2019 | Diederich et al. |
| 2019/0118005 A1 | 4/2019 | Diederich et al. |
| 2019/0175252 A1 | 6/2019 | Heggeness |
| 2019/0282268 A1 | 9/2019 | Pellegrino et al. |
| 2019/0290296 A1 | 9/2019 | Patel et al. |
| 2019/0298392 A1 | 10/2019 | Capote et al. |
| 2019/0365416 A1 | 12/2019 | Brockman et al. |
| 2020/0000480 A1 | 1/2020 | Alambeigi et al. |
| 2020/0022709 A1 | 1/2020 | Burger et al. |
| 2020/0030601 A1 | 1/2020 | Molnar et al. |
| 2020/0060695 A1 | 2/2020 | Purdy et al. |
| 2020/0060747 A1 | 2/2020 | Edidin |
| 2020/0069920 A1 | 3/2020 | Goshayeshgar |
| 2020/0078083 A1 | 3/2020 | Sprinkle et al. |
| 2020/0138454 A1 | 5/2020 | Patel et al. |
| 2020/0146743 A1 | 5/2020 | Defosset et al. |
| 2020/0146744 A1 | 5/2020 | Defosset et al. |
| 2020/0214762 A1 | 7/2020 | Pellegrino et al. |
| 2020/0281646 A1 | 9/2020 | Pellegrino et al. |
| 2021/0113238 A1 | 4/2021 | Donovan et al. |
| 2021/0113239 A1 | 4/2021 | Donovan |
| 2021/0177502 A1 | 6/2021 | Wright et al. |

FOREIGN PATENT DOCUMENTS

| | | |
|---|---|---|
| AU | 2008249202 | 9/2003 |
| AU | 2033218612 | 9/2003 |
| AU | 2009296474 | 9/2009 |
| AU | 2015234376 | 9/2009 |
| AU | 2018223007 | 9/2009 |
| AU | 2020201962 | 9/2009 |
| AU | 2011204278 | 1/2011 |
| AU | 2012362524 | 12/2012 |
| AU | 2019201705 | 12/2012 |
| AU | 2013337680 | 11/2013 |
| AU | 2019206037 | 11/2013 |
| AU | 2021200382 | 11/2013 |
| CA | 2397413 | 2/2001 |
| CA | 2723071 | 2/2001 |
| CA | 2443491 | 9/2003 |
| CA | 2737374 | 9/2009 |
| CA | 2957010 | 9/2009 |
| CA | 2785207 | 1/2011 |
| CA | 2889478 | 11/2013 |
| CA | 3093398 | 11/2013 |
| EP | 0040658 | 12/1981 |
| EP | 0584959 | 3/1994 |
| EP | 0597463 | 5/1994 |
| EP | 0880938 | 12/1998 |
| EP | 1013228 | 6/2000 |
| EP | 1059067 | 12/2000 |
| EP | 1059087 | 12/2000 |
| EP | 7010394 | 2/2001 |
| EP | 7010531.2 | 2/2001 |
| EP | 7010649.7 | 2/2001 |
| EP | 10012521 | 2/2001 |
| EP | 16197060.3 | 2/2001 |
| EP | 19053974 | 2/2001 |
| EP | 3256168 | 9/2003 |
| EP | 10012523.6 | 9/2003 |
| EP | 50215979 | 9/2003 |
| EP | 1294323 B1 | 4/2007 |
| EP | 1938765 A1 | 7/2008 |
| EP | 2092952 A1 | 8/2009 |
| EP | 9816892.5 | 9/2009 |
| EP | 18166323.8 | 9/2009 |
| EP | 1471836 | 4/2010 |
| EP | 1471836 B1 | 4/2010 |
| EP | 11732213.1 | 1/2011 |
| EP | 20161054.0 | 1/2011 |
| EP | 13852217.2 | 11/2013 |
| EP | 19162385.9 | 11/2013 |
| EP | 2759276 A1 | 7/2014 |
| EP | 2785260 | 8/2015 |
| EP | 2965782 | 1/2016 |

(56) References Cited

FOREIGN PATENT DOCUMENTS

| | | |
|---|---|---|
| EP | 2508225 | 9/2016 |
| EP | 3078395 | 10/2016 |
| EP | 2205313 | 11/2016 |
| EP | 3097946 | 11/2016 |
| EP | 2913081 | 1/2017 |
| HK | 8102841.9 | 2/2001 |
| HK | 8103900.5 | 2/2001 |
| HK | 12100034.4 | 9/2009 |
| HK | 19124269.2 | 9/2009 |
| HK | 13105656.9 | 1/2011 |
| HK | 16100183.9 | 11/2013 |
| IL | 220747 | 1/2011 |
| IL | 245665 | 1/2011 |
| IL | 238516 | 11/2013 |
| JP | S53-139791 | 11/1978 |
| JP | 6-47058 | 2/1994 |
| JP | 10-290806 | 11/1998 |
| JP | 2001-037760 | 2/2001 |
| JP | 2001-556439 | 2/2001 |
| JP | 2003-341164 | 9/2003 |
| JP | 2009-269652 | 9/2003 |
| JP | 2012-246075 | 9/2003 |
| JP | 10012523.6 | 9/2003 |
| JP | 2005-169012 | 6/2005 |
| JP | 2011-529245 | 9/2009 |
| JP | 2015-0210950 | 9/2009 |
| JP | 2016-201503 | 9/2009 |
| JP | 2018-008547 | 9/2009 |
| JP | 2012-548169 | 1/2011 |
| JP | 2013-1951 | 1/2011 |
| JP | 2015-540810 | 11/2013 |
| JP | 2017-156808 | 11/2013 |
| JP | 2018-232891 | 11/2013 |
| JP | 2021-026929 | 11/2013 |
| KR | 17108246.6 | 2/2001 |
| KR | 2003-0017897 | 3/2003 |
| WO | WO96/36289 | 11/1996 |
| WO | WO98/27876 | 7/1998 |
| WO | WO98/34550 | 8/1998 |
| WO | WO99/19025 | 4/1999 |
| WO | WO99/44519 | 9/1999 |
| WO | WO99/48621 | 9/1999 |
| WO | WO00/21448 | 4/2000 |
| WO | WO00/33909 | 6/2000 |
| WO | WO00/49978 | 8/2000 |
| WO | WO00/56237 | 9/2000 |
| WO | WO00/67648 | 11/2000 |
| WO | WO00/67656 | 11/2000 |
| WO | WO01/01877 | 1/2001 |
| WO | WO01/45579 | 6/2001 |
| WO | WO01/57655 | 8/2001 |
| WO | WO02/05699 | 1/2002 |
| WO | WO02/05897 | 1/2002 |
| WO | WO02/28302 | 4/2002 |
| WO | WO2002/026319 | 4/2002 |
| WO | WO02/054941 | 7/2002 |
| WO | WO02/067797 | 9/2002 |
| WO | WO02/096304 | 12/2002 |
| WO | WO 2006/044794 | 4/2006 |
| WO | WO 2007/001981 | 1/2007 |
| WO | WO 2007/008954 | 1/2007 |
| WO | WO07/031264 | 3/2007 |
| WO | WO08/001385 | 1/2008 |
| WO | WO08/008522 | 1/2008 |
| WO | WO 2008/076330 | 6/2008 |
| WO | WO 2008/076357 | 6/2008 |
| WO | WO08/121259 | 10/2008 |
| WO | WO 2008/121259 | 10/2008 |
| WO | WO2008/140519 | 11/2008 |
| WO | WO 2008/141104 | 11/2008 |
| WO | WO 2008/144709 | 11/2008 |
| WO | WO 2009/042172 | 4/2009 |
| WO | WO 2009/076461 | 6/2009 |
| WO | PCT/US2009/058329 | 9/2009 |
| WO | WO 2009/124192 | 10/2009 |
| WO | WO 2009/155319 | 12/2009 |
| WO | WO 2010/111246 | 9/2010 |
| WO | WO 2010/135606 | 11/2010 |
| WO | PCT/US2011/020535 | 1/2011 |
| WO | WO 2011/041038 | 4/2011 |
| WO | WO 2012/024162 | 2/2012 |
| WO | WO 2012/165753 | 3/2012 |
| WO | 2012/056753 A1 | 5/2012 |
| WO | 2012/074729 A1 | 6/2012 |
| WO | WO 2012/074932 | 6/2012 |
| WO | PCT/US2012/071465 | 12/2012 |
| WO | WO 2013/009516 | 1/2013 |
| WO | 2013/101772 A1 | 7/2013 |
| WO | WO 2013/134452 | 9/2013 |
| WO | PCT/US2013/068012 | 11/2013 |
| WO | WO 2013/168006 | 11/2013 |
| WO | WO 2013/180947 | 12/2013 |
| WO | WO 2014/004051 | 1/2014 |
| WO | WO 2014/130231 | 8/2014 |
| WO | WO 2014/141207 | 9/2014 |
| WO | WO 2014/165194 | 10/2014 |
| WO | WO 2014/176141 | 10/2014 |
| WO | WO 2015/038317 | 3/2015 |
| WO | WO 2015/047817 | 4/2015 |
| WO | WO 2015/066295 | 5/2015 |
| WO | WO 2015/066303 | 5/2015 |
| WO | WO 2015/079319 | 6/2015 |
| WO | 2015/119773 A1 | 8/2015 |
| WO | WO 2015/148105 | 10/2015 |
| WO | WO 2014/145222 | 1/2016 |
| WO | WO 2014/145659 | 1/2016 |
| WO | WO 2014/146029 | 1/2016 |
| WO | WO 2016/033380 | 3/2016 |
| WO | WO 2016/048965 | 3/2016 |
| WO | WO 2014/197596 | 4/2016 |
| WO | WO 2014/210373 | 5/2016 |
| WO | WO 2016/069157 | 5/2016 |
| WO | WO 2016/075544 | 5/2016 |
| WO | WO 2015/024013 | 6/2016 |
| WO | WO 2016/090420 | 6/2016 |
| WO | WO 2016/105448 | 6/2016 |
| WO | WO 2016/105449 | 6/2016 |
| WO | WO 2015/044945 | 8/2016 |
| WO | WO 2015/057696 | 8/2016 |
| WO | WO 2015/060927 | 8/2016 |
| WO | WO 2016/127130 | 8/2016 |
| WO | WO 2016/130686 | 8/2016 |
| WO | WO 2016/134273 | 8/2016 |
| WO | WO 2011/157714 | 9/2016 |
| WO | WO 2016/148954 | 9/2016 |
| WO | WO 2016/154091 | 9/2016 |
| WO | WO 2016/168381 | 10/2016 |
| WO | WO 2016/209682 | 12/2016 |
| WO | WO 2017/009472 | 1/2017 |
| WO | WO 2017/010930 | 1/2017 |
| WO | WO 2017/019863 | 2/2017 |
| WO | WO 2017/027703 | 2/2017 |
| WO | WO 2017/027809 | 2/2017 |
| WO | WO 2018/116273 | 6/2018 |
| WO | PCT/US2020/050249 | 9/2020 |
| WO | WO 2020/198150 | 10/2020 |
| WO | PCT/US2021/040843 | 7/2021 |

OTHER PUBLICATIONS

Australia, 774022, Msihods and Devices For Intimosseous Nerve Ablation.
Canada, 2,397,433, Methods and Devices For Intraosseous Nerve Ablation.
Canada, 2,723,071, Methods and Devices For Intraosseous Nerve Ablation.
Europe, Applicantion No. 1255500, Devices For Intraosseous Nerve Ablation.
Europe, Applicantion No. 1844723, Methods and Devices For Intraosseous Nerve Ablation.
Europe, Applicantion No. 1832244, Methods and Devices For Intraosseous Nerve Ablation.

(56) References Cited

OTHER PUBLICATIONS

Europe, Applicantion No. 3143958, Methods and Devices For Intraosseous Nerve Ablation.
Hong Kong, Applicantion No. 1109847, Methods and Devices For Intraosseous Nerve Ablation.
Hong Kong, Applicantion No. 1108671, Methods and Devices For Intraosseous Nerve Ablation.
Hong Kong, Applicantion No. 1234625, Devices For Intraosseous Nerve Ablation.
Japan, Applicantion No. 4916635, Methods and Devices For Intraosseous Nerve Ablation.
U.S. Appl. No. 10/401,854 U.S. Pat. No. 7,258,690, filed Mar. 28, 2023, Windowed Thermal Ablation Probe.
U.S. Appl. No. 15/845,699, filed Dec. 18, 2017, Thermal Denervation Devices and Methods.
U.S. Appl. No. 16/153,407 U.S. Pat. No. 10,463,423, filed Oct. 5, 2018, Thermal Denervation Devices and Methods.
U.S. Appl. No. 14/535,868 U.S. Pat. No. 9,848,944, filed Nov. 7, 2014, Thermal Denervation Devices and Methods.
U.S. Appl. No. 11/123,766 U.S. Pat. No. 7,749,238, filed May 6, 2005, Method of Straddling An Intraosseous Nerve.
U.S. Appl. No. 14/136,763 U.S. Pat. No. 9,023,038, filed Dec. 20, 2013, Denewation Methods.
U.S. Appl. No. 14/174,024 U.S. Pat. No. 9,017,325, filed Jan. 3, 2014, Nerve Modulation Systems.
U.S. Appl. No. 14/153,922 U.S. Pat. No. 9,173,676, filed Jan. 13, 2014, Nerve Modulation Systems.
U.S. Appl. No. 14/695,330 U.S. Pat. No. 9,421,064, filed Apr. 24, 2015, Nerve Modulation Systems.
U.S. Appl. No. 14/701,908, filed May 1, 2015, Denewation Methods.
U.S. Appl. No. 14/928,037 U.S. Pat. No. 10,028,753, filed Oct. 30, 2015, Intraosseous Nerve Modulation Methods.
U.S. Appl. No. 15/241,523 U.S. Pat. No. 9,724,107, filed Aug. 19, 2016, Newe Modulation Systems.
U.S. Appl. No. 15/669,399 U.S. Pat. No. 10,905,440, filed Aug. 4, 2017, Newe Modulation Systems.
U.S. Appl. No. 16/152,834, filed Oct. 5, 2018, Bipolar Radiofrequency Ablation Systems For Treament Within Bone.
U.S. Appl. No. 16/156,850, filed Oct. 10, 2018, Systems For Treating Nerves Within Bone Using Steam.
U.S. Appl. No. 16/747,830, filed Jan. 21, 2020, Danewamm Methods.
U.S. Appl. No. 14/673,172 U.S. Pat. No. 9,486,279 filed Mar. 30, 2015, Intraosseous Nerve Treatment.
U.S. Appl. No. 15/344,284 U.S. Pat. No. 10,111,704, filed Nov. 4, 2016, Intraosseous Nerve Treatment
U.S. Appl. No. 16/153,234 U.S. Pat. No. 10,478,246, filed Oct. 5, 2018, Abiation of Tissue Withinl Vertebral Body Involving Internal Cooling.
U.S. Appl. No. 16/153,242 U.S. Pat. No. 10,588,691, filed Oct. 5, 2018, Radiofrequency Abiation of Tissue Within Vertebral Body.
U.S. Appl. No. 16/160,155, filed Oct. 15, 2018, Intraosseous Nerve Treatment.
U.S. Appl. No. 16/818,092, filed Mar. 13, 2020, Radiofrequency Abiation Of Tissue Within Vertebral Body.
U.S. Appl. No. 17/394,189, filed Aug. 4, 2021, Radiofrequency Abiation of Tissue Within Vertebral Body.
U.S. Appl. No. 17/394,166, filed Aug. 4, 2021, Radiofrequency Abiation Of Tissue Within Vertebral Body.
U.S. Appl. No. 13/541,591 (Reissue of U.S. Pat. No. 7,749,218) RE46356, filed Jul. 3, 2012, Method of Treating an Intraosseous Nerve.
U.S. Appl. No. 15/469,315 (Reissue of U.S. Pat. No. 7,749,218) RE48460, filed Mar. 24, 2017, Method of Treating an Intraosseous Nerve.
U.S. Appl. No. 16/153,598 (Reissue of U.S. Pat. No. 7,749,218), filed Oct. 5, 2018, Method of Treating an Intraosseous Nerve.
U.S. Appl. No. 16/153,603 (Reissue of U.S. Pat. No. 7,749,218), filed Oct. 5, 2018, Method of Treating an Intraosseous Nerve.

U.S. Appl. No. 17/193,491, filed Mar. 5, 2021, Method of Treating an Intraosseous Nerve.
U.S. Appl. No. 15/040,268 U.S. Pat. No. 10,265,099, filed Feb. 10, 2016, Systems for Accessing Nerves Within Bone.
U.S. Appl. No. 16/368,453, filed Mar. 29, 2019, Systems for Accessing Nerves Within Bone.
U.S. Appl. No. 12/868,818 U.S. Pat. No. 8,808,234, filed Aug. 26, 2010, Systems for Navigariing an Instrument Through Bone.
U.S. Appl. No. 14/462,371 U.S. Pat. No. 9,265,522, filed Aug. 18, 2014, Systems for Navigariing an instrument Through Bone.
U.S. Appl. No. 13/543,723 U.S. Pat. No. 3,414,571, filed Jul. 6, 2012, Vertebral Bone Navigation Systems.
U.S. Appl. No. 16/205,050, filed Nov. 29, 2018, Methods of Demrvating Vertebral Body Using External Energy Source.
U.S. Appl. No. 14/440,050 U.S. Pat. No. 9,775,627, filed Apr. 30, 2015, Systems and Methods for Creating Curved Paths Throuugh Bone and Modulating Nerves Within The Bone.
U.S. Appl. No. 15/722,392 U.S. Pat. No. 10,357,258, filed Oct. 2, 2017, Systems and Methods for Creating Curved Paths Throuugh Bone and Modulating Nerves Within The Bone.
U.S. Appl. No. 16/370,264 U.S. Pat. No. 10,517,611, filed Mar. 29, 2019, Systems for Navigation And Treatment Within A Vertebral Body.
U.S. Appl. No. 16/717,985 U.S. Pat. 11,160,563, filed Dec. 17, 2019, Systems for Navigation And Treatment Within A Vertebral Body.
U.S. Appl. No. 17/488,116, filed Sep. 28, 2021, Systems for Navigation And Treatment Within a Vertebral Body.
U.S. Appl. No. 17/488,111, filed Sep. 28, 2021, Methods of Navigation And Treatment Within a Vertebral Body.
U.S. Appl. No. 14/454,643 U.S. Pat. No. 9,724,151, filed Aug. 7, 2014, Modulating Nerves Within Bone Using Bone Fasteners.
U.S. Appl. No. 15/669,292, filed Aug. 4, 2017, Modulating Nerves Within Bone Using Bone Fasteners.
U.S. Appl. No. 16/661,271 U.S. Pat. No. 11,065,046, filed Oct. 23, 2019, Modulating Nerves Within Bone Using Bone Fasteners.
U.S. Appl. No. 17/378,457, filed Jul. 16, 2021, Modulating Nerves Within Bone.
U.S. Appl. No. 17/138,203 U.S. Pat. No. 11,123,103, filed Dec. 30, 2020, Introducer Systems for Bone Access.
U.S. Appl. No. 17/138,234 U.S. Pat. No.11,007,010, filed Dec. 30, 2020, Curved Bone Access Systems.
U.S. Appl. No. 17/302,949 U.S. Pat. No. 11,202,655, filed Mar. 17, 2021, Accessing and Treating Tissue Within a Vertical Body.
U.S. Appl. No. 17/303,254, filed Mar. 25, 2021, Methods of Treating a Vertical Body.
U.S. Appl. No. 17/303,267 U.S. Pat. No. 11,207,100, filed Mar. 25, 2021, Methods of Detecting and Treating Back Pain.
U.S. Appl. No. 17/449,051, filed Sep. 27, 2021, Introducer Bill.
A Novel Approach for Treating Chronic Lower Back Pain Abstract for Presentation at North American Spine Society 26th Annual Meeting in Chicago IL on Nov. 4, 2011.
Antonacci M. Darryl et al.; Innervation of the Human Vertebral Body: A Histologic Study: Journal of Spinal Disorder vol. 11 No. 6 pp. 526-531 1998 Lippincott Williams & Wilkins Philadelphia.
Arnoldi Carl C.; Intraosseous Hypertension—A Possible Cause of Low Back Pain?; Clinical Orthopedics and Related Research No. 115 Mar.-Apr. 1976.
Bailey, Jeannie F., "Innervation Patterns of PGP 9.5-Positive Nerve Fibers within the Human Lumbar Vertebra," Journal of Anatomy, (2011) 218, pp. 263-270, San Francisco, California.
Becker, Stephan, et al., "Ablation of the basivertebral nerve for treatment of back pain: a clinical study," The Spine Journal, vol. 17, pp. 218-223 (Feb. 2017).
Bergeron et al. "Fluoroscopic-guided radiofrequency ablation of the basivertebral nerve: application and analysis with multiple imaging modalities in an ovine model" Thermal Treatment of Tissue: Energy Delivery and Assessment III edited by Thomas P. Ryan Proceedings of SPIE vol. 5698 (SPIE Bellingham WA 2005) pp. 156-167.
Bogduk N. The anatomy of the lumbar intervertebral disc syndrome Med J. Aust. 1976 vol. 1 No. 23 pp. 878-881.

(56) References Cited

OTHER PUBLICATIONS

Bogduk Nikolai et al.; Technical Limitations to the efficacy of Radiofrequency Neurotomy for Spinal Pain; Neurosurgery vol. 20 No. 4 1987.
Caragee, EG et al.; "Discographic, MRI and psychosocial determinants of low back pain disability andremission: A prospective study in subjects with benign persistent back pain", The Spine Journal: The Official Journal of the North American Spine Society, vol. 5(1), pp. 24-35 (2005).
Choy Daniel SS.J. et al.; Percutaneous Laser Disc Decompression A New Therapeutic Modality; SPINE vol. 17 No. 8 1992.
Cosman E.R. et al. Theoretical Aspects of Radiofrequency Lesions in the Dorsal Root Entry Zone. Neurosurgery vol. 1 No. 6 1984 pp. 945-950.
Deardorff Dana L. et al.; Ultrasound applicators with internal cooling for interstitial thermal therapy; SPIE vol. 3594 1999.
Deramond H. et al. Temperature Elevation Caused by Bone Cement Polymerization During Vertebroplasty Bone Aug. 1999 pp. 17S-21S vol. 25 No. 2 Supplement.
Diederich C. J. et al. "IDTT Therapy in Cadaveric Lumbar Spine: Temperature and thermal dosedistributions Thermal Treatment of Tissue: Energy Delivery and Assessment" Thomas P. Ryan Editor Proceedings of SPIE vol. 4247:104-108 (2001).
Diederich Chris J. et al.; Ultrasound Catheters for Circumferential Cardiac Ablation; SPIE vol. 3594 (1999).
Dupuy D.E. et al. Radiofrequency ablation of spinal tumors: Temperature distribution in the spinal canal AJR vol. 175 pp. 1263-1266 Nov. 2000.
Dupuy Damian E.; Radiofrequency Ablation: An Outpatient Percutaneous Treatment; Medicine and Health/Rhode Island vol. 82 No. Jun. 6, 1999.
Esses Stephen I. et al.; Intraosseous Vertebral Body Pressures; SPINE vol. 17 No. 6 Supplement 1992.
FDA Response to 510(k) Submission by Relievant Medsystems Inc. submitted on Sep. 27, 2007 (date stamped on Oct. 5, 2007) and associated documents.
Fras M.D. Christian et al. "Substance P-containing Nerves within the Human Vertebral Body: An Immunohistochemical Study of the Basivertebral Nerve" The Spine Journal 3 2003 pp. 63-67RE.
Fields, AJ et al; "Innervation of pathologies in the lumbar vertebral endplate and intervertebral disc". The Spine Journal: Official Journal of the North American Spine Society, vol. 14(3), pp. 513-521 (2014).
Fields, Aaron J. et al.; "Cartilage endplate damage strongly assocates with chronic low back pain, independent of modic changes", Abstract form Oral Presentation at the ISSLS Annual Meeting in Banff, Canada (May 14-18, 2018).
Fischgrund JS, et al.; "Intraosseous Basivertebral Nerve Ablation for the Treatment of Chronic LowBack Pain: 2-Year Results from a Prospective Randomized Double-Blind Sham-Controlled Multicenter Study", International Journal of Spine Surgery, vol. 13 (2), pp. 110-119 (2019).
Fras M.D., Christian et al., "Substance p. containing Nerves within the Human Vertebral Body: An Immunohistochemical Study of the Basivertebral Nerve", The Spine Journal 3, 2003, pp. 63-67.
Geht J. "Electroporation: theory and methods perspectives for drug delivery gene therapy and research" Acta Physiol. Scand. vol. 177 pp. 437-447 (2003).
Goldberg S.N. et al. Tissue ablation with radiofrequency: Effect of probe size gauge duration and temperature on lesion Volume Acad. Radiol. vol. 2 pp. 399-404 (1995).
Gornet, Matthew G et al.; "Magnetic resonance spectroscopy (MRS) can identify painful lumbar discsand may facilitate improved clinical outcomes of lumbar surgeries for discogenic pain", European Spine Journal, vol. 28, pp. 674-687 (2019).
Hanal Kenji et al.; Simultaneous Measurement of Intraosseous and Cerebrospinal Fluid Pressures in the Lumbar Region; SPINE vol. 10 No. 1 1985.

Heggeness Michael H. et al. The Trabecular Anatomy of Thoracolumbar Vertebrae: Implications for Burst Fractures Journal of Anatomy 1997 pp. 309-312 vol. 191 Great Britain.
Heggeness Michael H. et al. Discography Causes End Plate Deflection; SPINE vol. 18 No. 8 pp. 1050-1053 1993 J.B. Lippincott Company.
Heggeness, M. et al Ablation of the Basivertebral Nerve for the Treatment of Back Pain: A Pilot Clinical Study; The Spine Journal, 2011, vol. 11, Issue 10, Supplement, pp. S65-S66, ISSN 1529-9430.
Hoopes et al. "Radiofrequency Ablation of The Basivertebral Nerve as a Potential Treatment of Back Pain: Pathologic Assessment in an Ovine Model" Thermal Treatment of Tissue: Energy Delivery and Assessment III edited by Thomas P. Ryan Proceedings of SPIE vol. 5698 (SPIE Bellingham WA 2005) pp. 168-180.
Houpt Jonathan C. et al.; Experimental Study of Temperature Distributions and Thermal TransportDuring Radiofrequency Current Therapy of the Intervertebral Disc; SPINE vol. 21 No. 15 pp. 1808-1813 1996 Lippincott-Raven Publishers.
Jourabchi, Natanel et al.; "Irreversible electroporation (NanoKnife) in cancer treatment," Gastrointestinal Intervention, vol. 3, pp. 8-18 (2014).
Khalil, J et al.; "A Prospective, Randomized, Multi-Center Study of Intraosseous Basivertebral Nerve Ablation for the Treatment of Chronic Low Back Pain", The Spine Journal (2019), avilable at https://doi.org/10.1016/jspinee.2019.05.598.
Kleinstueck Frank S. et al.; Acute Biomechanical and Histological Effects of Intradiscal Electrothermal Therapy on Human Lumbar Discs; SPINE vol. 26 No. 20 pp. 2198-2207; 2001 Lippincott Williams & Wilkins Inc.
Kopecky Kenyon K. et al. "Side-Exiting Coaxial Needle for Aspiration Biopsy"—AJR—1996; 167 pp. 661-662.
Kuisma M et al.; "Modic changes in endplates of lumbar vertebral bodies: Prevalence and associationwith low back and sciatic pain among middle-aged male workers", Spine, vol. 32(10), pp. 1116-1122 (2007).
Lehmann Justus F. et al.; Selective Heating Effects of Ultrasound in Human Beings; Archives of Physical Medicine & Rehabilitation Jun. 1966.
Letcher Frank S. et al.; The Effect of Radiofrequency Current and Heat on Peripheral Nerve Action Potential in the Cat; U.S. Naval Hospital Philadelphia PA. (1968).
Lotz JC, et al.; "The Role of the Vertebral End Plate in Low Back Pain", Global Spine Journal, vol. 3, pp. 153-164 (2013).
Lundskog Jan; Heat and Bone Tissue-/an experimental investigation of the thermal properties of bone tissue and threshold levels for thermal injury; Scandinavian Journal of Plastic and Reconstructive Surgery Supplemental 9 From the Laboratory of Experimental Biology Department of anatomy University of Gothenburg Gothenburg Sweden Goteborg 1972.
Martin J.B. et al. Vertebroplasty: Clinical Experience and Follow-up Results Bone Aug. 1999 pp. 11S-15S vol. 25 No. 2 Supplement.
Massad Malek M.D. et al.; Endoscopic Thoracic Sympathectomy: Evaluation of Pulsatile Laser Non-Pulsatile Laser and Radiofrequency-Generated Thermocoagulation; Lasers in Surgery and Medicine; 1991; pp. 18-25.
Mehta Mark et al.; The treatment of chronic back pain; Anaesthesia 1979 vol. 34 pp. 768-775.
Modic MT et al.; "Degenerative disk disease: assessment of changes in vertebral body marrow with MR imaging" Radiology vol. 166 pp. 193-199 (1988).
Mok, Florence et al.; "Modic changes of the lumbar spine: Prevalence, risk factors, and association withdisc degeneration and low back pain in a large-scale population-based cohort", The Spine Journal: Official Journal of the North American Spine Society, vol. 16(1), pp. 32-41 (2016).
Nau William H. Ultrasound interstitial thermal therapy (USITT) in the prostate; SPIE vol. 3594 Jan. 1999.
Osteocool Pain Management Brochure, Baylis Medical, copyright 2011.
Pang, Henry et al,; The UTE Disc Sign on MRI: A Novel Imaging Biomarker Associated With Degenerative Spine Changes, Low Back Pain, and Disability, SPINE, vol. 42 (Aug. 2017).

(56) References Cited

OTHER PUBLICATIONS

Radiological Society of North America. "Pulsed radiofrequency relieves acute back pain and sciatica." ScienceDaily, ScienceDaily, Nov. 27, 2018. <www.sciencedaily.com/releases/2018/11/181127092604.htm>.
Rashbaum Ralph F.; Radiofrequency Facet Denervation A Treatment alternative in Refractory Low Back Pain with or without Leg Pain; Orthopedic Clinics of North America—vol. 14 No. 3 Jul. 1983.
Rosenthal D.I. Seminars in Musculoskeletal Radiology vol. 1 No. 2. pp. 265-272 (1997).
Ryan et al. "Three-Dimensional Finite Element Simulations of Vertebral Body Thermal Treatment" Thermal Treatment of Tissue: Energy Delivery and Assessment III edited by Thomas P. Ryan Proceedings of SPIE vol. 5698 (SPIE Bellingham WA 2005) pp. 137-155.
Shealy C. Norman; Percutaneous radiofrequency denervation of spinal facets Treatment for chronic back pain and sciatica; Journal of Neurosurgery/vol. 43/Oct. 1975.
Sherman Mary S.; The Nerves of Bone The Journal of Bone and Joint Surgery Apr. 1963 pp. 522-528 vol. 45-A No. 3.
Solbiati L. et al. Hepatic metastases: Percutaneous radio-frequency ablation with cooled-tip electrodes. Interventional Radiology vol. 205 No. 2 pp. 367-373 (1997).
Stanton Terry "Can Nerve Ablation Reduce Chronic Back Pain?" AAOS Now Jan. 2012.
The AVAmax System—Cardinal Health Special Procedures Lit. No. 25P0459-01—www.cardinal.com (copyright 2007).
Tillotson L. et al. Controlled thermal injury of bone: Report of a percutaneous technique using radiofrequency electrode and generator. Investigative Radiology Nov. 1989 pp. 888-892.
Troussier B. et al.; Percutaneous Intradiscal Radio-Frequency Thermocoagulation A Cadaveric Study; SPINE vol. 20 No. 15 pp. 1713-1718 1995 Lippincott-Raven Publishers.
Ullrich Jr. Peter F. "Lumbar Spinal Fusion Surgery" Jan. 9, 2013 Spine-Health (available viawayback machine Internet archive at http://web.archive.org/web/20130109095419/http://www/spine-health.com/treatment/spinal-fusion/lumbar-spinal-fusion-surgery).
Weishaupt, D et al,; "Painful Lumbar Disk Derangement: Relevance of Endplate Abnormalities at MR Imaging", Radiology, vol. 218(2), pp. 420-427 (2001).
YouTube Video, "DFINE-STAR Procedure Animation," dated Sep. 30, 2013, can be viewed at https://www.youtube.com/watch?v=YxtKNyc2e-0.
Kim et al., Transforaminal epiduroscopic basivertebral nerve laser ablation for chronic low back pain associated with modic changes: A preliminary open-label study. Pain Research and Management 2018; https://pubmed.ncbi.nlm.nih.gov/30186540.
Rahme et al., The modic vertebral endplate and marrow changes: pathologic significance and relation to low back pain and segmental instability of the lumbar spine. American Journal of Neuroradiology 29.5 (2008): 838-842; http://www.ajnr.org/content/29/5/838.
Peter F. Ullrich, Jr., MD, Lumbar Spinal Fusion Surgery, Jan. 9, 2013, Spine-Health.
U.S. Appl. No. 09/775,137 U.S. Pat No. 6,699,242, filed Feb. 1, 2001, Methods and Devices for Intraosseous Nerve Ablation.
U.S. Appl. No. 10/103,439 U.S. Pat. No. 6,736,835, filed Mar. 21, 2002, Novel Early Intervention Spinal Treatment Methods and Devices for Use Therein.
U.S. Appl. No. 10/260,879 U.S. Pat. No. 6,907,884, filed Sep. 30, 2002, Method of Straddling an Intraosseous Nerve.
U.S. Appl. No. 10/401,854 U.S. Pat. No. 7,258,690, filed Mar. 28, 2003, Windowed Thermal Ablation Probe.
U.S. Appl. No. 11/123,766 U.S. Pat. No. 7,749,218, filed May 6, 2005, Method of Straddling an Intraosseous Nerve.
U.S. Appl. No. 11/745,446, filed May 7, 2007, Windowed Thermal Ablation Probe.
U.S. Appl. No. 12/566,895 U.S. Pat. No. 8,419,730, filed Sep. 25, 2009, Systems and Methods for Navigating an Instrument Through Bone.
U.S. Appl. No. 12/643,997, filed Dec. 21, 2009, Windowed Thermal Ablation Probe.
U.S. Appl. No. 12/683,555 U.S. Pat. No. 8,613,744, filed Jan. 7, 2010, Systems and Methods for Navigating an Instrument Through Bone.
U.S. Appl. No. 12/868,818 U.S. Pat. No. 8,808,284, filed Aug. 26, 2010, Systems for Navigating an Instrument Through Bone.
U.S. Appl. No. 13/541,591 (Reissue of U.S. Pat. No. 7,749,218), filed Jul. 3, 2012, Method of Treating an Intraosseous Nerve.
U.S. Appl. No. 13/543,712 U.S. Pat. No. 8,535,309, filed Jul. 6, 2012, Vertebral Bone Channeling Systems.
U.S. Appl. No. 13/543,721, filed Jul. 6, 2012, Intraosseous Nerve Denervation Methods.
U.S. Appl. No. 13/543,723 U.S. Pat. No. 8,414,571, filed Jul. 6, 2012, Vertebral Bone Navigation Systems.
U.S. Appl. No. 13/612,541 U.S. Pat. No. 8,361,067, filed Sep. 12, 2012, Methods of Therapeutically Heating a Vertebral Body to Treat Back Pain.
U.S. Appl. No. 13/612,561 U.S. Pat. No. 8,425,507, filed Sep. 12, 2012, Basivertebral Nerve Denervation.
U.S. Appl. No. 13/615,001 U.S. Pat. No. 8,419,731, filed Sep. 13, 2012, Methods of Treating Back Pain.
U.S. Appl. No. 13/615,300, filed Sep. 13, 2012, System for Heating a Vertebral Body to Treat Back Pain.
U.S. Appl. No. 13/617,470 U.S. Pat. No. 8,623,014, filed Sep. 14, 2012, Systems for Denervation of Basivertebral Nerves.
U.S. Appl. No. 13/655,683 U.S. Pat. No. 8,882,764, filed Oct. 19, 2012, Thermal Denervation Devices.
U.S. Appl. No. 13/862,242 U.S. Pat. No. 9,259,241, filed Apr. 12, 2013, Systems for Accessing Nerves Within Bone.
U.S. Appl. No. 13/862,306 U.S. Pat. No. 8,628,528, filed Apr. 12, 2013, Vertebral Denervation.
U.S. Appl. No. 13/862,317 U.S. Pat. No. 8,992,522, filed Apr. 12, 2013, Back Pain Treatment Methods.
U.S. Appl. No. 13/923,798 U.S. Pat. No. 8,992,523, filed Jun. 12, 2013, Vertebral Treatment.
U.S. Appl. No. 13/963,767 U.S. Pat. No. 9,039,701, filed Aug. 9, 2013, Channeling Paths Into Bone.
U.S. Appl. No. 14/136,763 U.S. Pat. No. 9,023,038, filed Dec. 20, 2013, Denervation Methods.
U.S. Appl. No. 14/153,922 U.S. Pat. No. 9, 173,676, filed Jan. 13, 2014, Nerve Modulation Methods.
U.S. Appl. No. 14/369,661 U.S. Pat. No. 10,390,877, filed Jun. 27, 2014, Systems and Methods for Treating Back Pain.

\* cited by examiner

MODULATING NERVES WITHIN BONE

INCORPORATION BY REFERENCE TO ANY PRIORITY APPLICATIONS

This application is a continuation of U.S. application Ser. No. 16/661,271 filed Oct. 23, 2019, now issued as U.S. Pat. No. 11,065,046, which is a continuation of U.S. application Ser. No. 15/669,292 filed Aug. 4, 2017, now issued as U.S. Pat. No. 10,456,187, which is a continuation of U.S. application Ser. No. 14/454,643 filed Aug. 7, 2014, now issued as U.S. Pat. No. 9,724,151, which claims the benefit of priority to U.S. Provisional Application No. 61/863,821 filed Aug. 8, 2013. Any and all applications for which a foreign or domestic priority claim is identified in the Application Data Sheet as filed with the present application are hereby incorporated by reference under 37 CFR 1.57.

FIELD

Various embodiments of the invention pertain generally to modulating nerves within bone (e.g., intraosseous nerves) using pre-existing hardware (e.g., implants, screws), and more particularly to modulation of basivertebral nerves within vertebral bodies of the spine.

BACKGROUND

Back pain is a very common health problem worldwide and is a major cause for work-related disability benefits and compensation. Back pain may arise from strained muscles, ligaments, or tendons in the back and/or structural problems with bones or spinal discs. The back pain may be acute or chronic. Treatments for chronic back pain vary widely and include physical therapy and exercise, chiropractic treatments, rest, pharmacological therapy such as pain relievers or anti-inflammatory medications, and surgical intervention such as vertebral fusion, discectomy or disc repair. Existing treatments can be costly, addictive, temporary, ineffective, and/or can increase the pain or require long recovery times.

SUMMARY

Several embodiments of the invention are directed to the use of pre-existing implants in the body to facilitate energy delivery. The energy delivery (e.g., radiofrequency energy or other thermal energy) is used for neuromodulation (such as stimulation or denervation), tissue heating and ablation (including tumor ablation), curing, and other applications in the spine and non-spine orthopedic locations. Energy delivery to non-orthopedic locations is also contemplated herein. In addition to the use of pre-existing implants, temporary instruments placed in the body may also facilitate energy delivery according to several embodiments disclosed herein.

Implants or other hardware used as conductive devices according to embodiments described herein include, but are not limited to, bone screws, bone anchors, fastening devices, fusion devices, cages, nails, support plates, and other devices that possess conductive properties. Applications include, but are not limited to, the spine, knee, shoulder, hip, cranial bone, and small joints.

In several embodiments of the invention, pedicle screws or other implants or devices having at least a portion located within a vertebral body or other target bone can be used to deliver energy or agents to modulate nerves within the vertebral body or other target bone locations.

The terms "modulation" or "neuromodulation", as used herein, shall be given their ordinary meaning and shall also include ablation, permanent denervation, temporary denervation, disruption, blocking, inhibition, therapeutic stimulation, diagnostic stimulation, inhibition, necrosis, desensitization, or other effect on tissue. Neuromodulation shall refer to modulation of a nerve (structurally and/or functionally) and/or neurotransmission. Modulation is not limited to nerves and may include effects on other tissue.

Several embodiments of the invention have one or more of the following advantages as compared to direct application of energy (i) more diffuse, but controlled, heating can occur, (ii) energy is not applied directly to tissue (which may be beneficial when direct contact of an electrode to tissue is not desired), (iii) energy can be delivered to a tortuous (e.g., curved) and/or remote area where direct access to an electrode or other energy source may not be desirable), and (iv) because a pre-existing implant is used, an additional incision or pathway need not be created.

In some embodiments, one or more sensors are provided to detect the amount of energy delivered to the target and/or temperature of the target tissue. The sensors may include transducers, thermocouples, thermistors, and/or the like.

In several embodiments, specific bone screws having specialized conductive and/or insulating elements are used. For example, bone screws having insulating elements along the length except for a distal end portion or tip such that only the distal end portion or tip of the bone screw delivers heat or energy to the bone are used, thereby providing controlled delivery of energy to the bone. However, in many embodiments, the pre-existing implant (with no special adaptations) is used.

In some embodiments, the pre-existing implant (e.g., a bone screw) may be used as a guide to align and facilitate navigation of an independent energy delivery device.

In some embodiments, a bone screw or other anchor or fastening member is a primary means of conducting heat to nerves within bone without any intervening structures or other implantable devices (e.g., implantable stimulators). In some embodiments, one or more electrodes are placed in contact with one or more pre-existing implants (e.g., bone screws or other extant hardware) to effect neuromodulation (e.g., through heat, or thermal energy) instead of the electrodes directly contacting the tissue to be heated or stimulated. In some embodiments, energy is applied to the pre-existing implants during a single procedure and not as series of procedures repeated over a duration of time; however, in some embodiments, energy may be applied on more than one occasion.

In accordance with several embodiments, a method of treating back pain of a subject comprises performing a spinal fusion procedure between two adjacent vertebral bodies. The method may comprise inserting a distal end of a first pedicle screw within a cancellous bone region of a first vertebral body; and applying thermal energy to the first pedicle screw to conduct heat to the cancellous bone region sufficient to modulate a nerve within the cancellous bone region of the first vertebral body. In one embodiment, the method comprises inserting a distal end of a second pedicle screw within the cancellous bone region of the first vertebral body and applying thermal energy to the second pedicle screw to conduct heat to the cancellous bone region of the first vertebral body sufficient to modulate the nerve within the cancellous bone region of the first vertebral body in combination with the applied thermal energy to the first pedicle screw. In one embodiment, the method comprises inserting a distal end of a distal end of a pedicle screw (either a second pedicle screw or a third pedicle screw) within the cancellous bone region of a second vertebral body and applying thermal energy to the pedicle screw to conduct heat to the cancellous bone region of the second vertebral body sufficient to modulate a nerve within the cancellous bone region of the second vertebral body. The thermal energy may be applied to the various pedicle screws successively or simultaneously, or a combination of both (e.g., two at a time).

In accordance with several embodiments, a method of applying energy to the body comprises identifying a pre-existing implant proximate a region of interest. In one embodiment, the pre-existing implant comprises a conductive material. The region of interest may comprise a nerve within or proximate a bone. In one embodiment, the method comprises applying thermal energy to the pre-existing implant to conduct heat to the region of interest sufficient to modulate the nerve within or proximate the bone. For example, the bone may be a vertebral body and the nerve may be a basivertebral nerve within the vertebral body. The bone may alternatively be a bone of the shoulder, hip, cranium, wrist, arm, hand, knee, elbow, small joints, or other bone. In one embodiment, the region of interest is within a cancellous bone portion. In one embodiment, the region of interest is within or proximate a periosteal or osteal portion of the bone. The thermal energy may be applied using a radiofrequency energy delivery device coupled to and powered by a radiofrequency generator or other energy source. The energy delivery device may comprise one or more electrodes to deliver the thermal energy. The electrodes may be coupled to the energy source via one or more electrical wires or leads.

In accordance with several embodiments, a method of treating back pain in a subject having a pedicle screw inserted within a cancellous bone region of a vertebral body comprises identifying a pedicle screw proximate a region of interest. The pedicle screw may comprise a conductive material. At least a portion of the pedicle screw may be in contact with a cancellous bone region and the region of interest may comprise a nerve within the cancellous bone region. In one embodiment, the method comprises applying thermal energy to the pedicle screw to conduct heat to the cancellous bone of the vertebral body sufficient to modulate the nerve within the cancellous bone region. In one embodiment, the temperature of the thermal energy is between about 75 degrees Celsius and about 100 degrees Celsius. The thermal energy may be applied for a period of about 10 seconds to about 30 minutes (e.g., 10 seconds to 30 seconds, 20 seconds to 60 seconds, 30 seconds to 2 minutes, 1 minute to 5 minutes, 5 minutes to 15 minutes, 10 minutes to 30 minutes, 15 minutes to 30 minutes, or overlapping ranges thereof). In one embodiment, the applied thermal energy is sufficient to denervate the nerve. In one embodiment, the applied thermal energy is sufficient to ablate the nerve to permanently treat back pain associated with the nerve. The thermal energy may be applied using a heat source, such as a radio-frequency generator.

The methods summarized above and set forth in further detail below describe certain actions taken by a practitioner; however, it should be understood that they can also include the instruction of those actions by another party. Thus, actions such as "For example, actions such as "applying thermal energy" include "instructing the applying of thermal energy." Further aspects of embodiments of the invention will be discussed in the following portions of the specification. With respect to the drawings, elements from one figure may be combined with elements from the other figures.

BRIEF DESCRIPTION OF THE DRAWINGS

Several embodiments of the invention will be more fully understood by reference to the following drawings which are for illustrative purposes only.

DETAILED DESCRIPTION

Several embodiments of the invention are directed to systems and methods for modulating one or more nerves within bone using a previously inserted implant (such as a bone fastener or anchor member or other hardware that is already extant). In some embodiments, an intraosseous nerve within a vertebral body of the spine is modulated using one or more fasteners (e.g., pedicle screws) previously inserted within the vertebral body. For example, heat or thermal energy can be applied to a pedicle screw (e.g., using a heat source) and thermal energy may be conducted by heat transfer to one or more intraosseous nerves (e.g., a basivertebral nerve believed to be contributing to back pain) within the cancellous bone region of the vertebral body.

In accordance with several embodiments of the inventions, nerve modulation is performed in combination with, or in conjunction with, spinal fusion or spinal stabilization to treat back pain. The neuromodulation may be performed contemporaneously with the spinal fusion or during a separate treatment procedure. Although the systems and methods described herein are primarily directed to modulation of a basivertebral nerve of a vertebral member, the treatment may be applied to any nerve and/or to any tissue segment of the body (e.g., tumors or tissue growths within bone).

Figure 1:
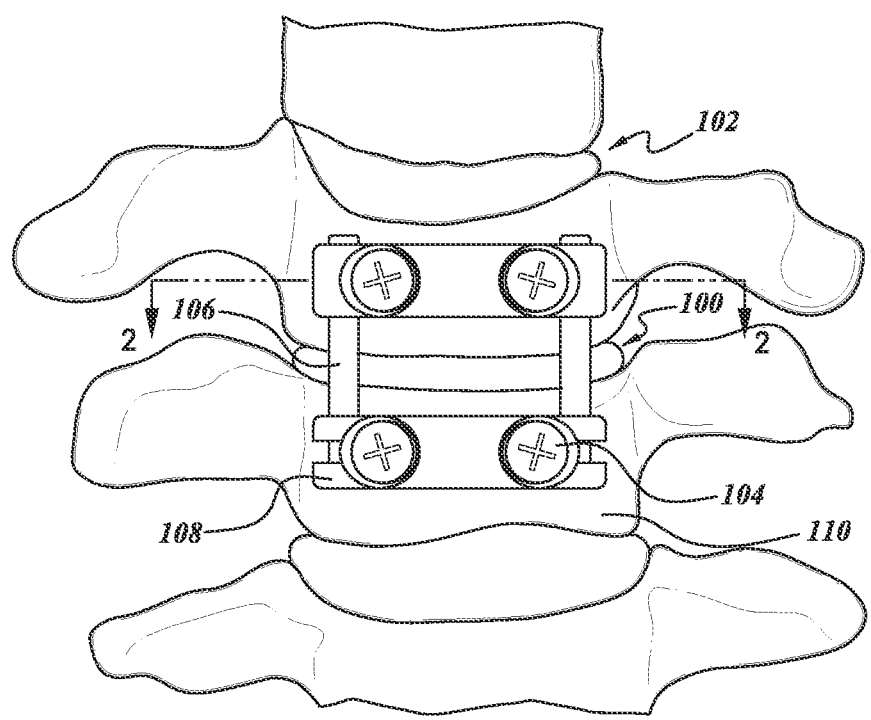
FIG. 1 illustrates a pedicle screw system connected to a portion of a human spine.

FIG. 1 illustrates a pedicle screw assembly 100 connected to a portion of a human spine 102. For example, the pedicle screw assembly 100 may be connected to the spine 102 during a spinal fusion or spinal stabilization procedure. The pedicle screw assembly 100 comprises multiple pedicle screws 104, multiple interconnected rods 106 and multiple plates or members 108. In some embodiments, the pedicle screws 104 are inserted through a pedicle or other bony portion of the spine 102 and into an inner cancellous bone region of a vertebral body 110. The pedicle screw assembly 100 may be used to stabilize a portion of the spine (e.g., one or more spine segments or levels) or to repair spinal defects (e.g., scoliosis, herniated discs, fractures, etc.). During a spinal fusion or stabilization procedure, fusion or graft material may be inserted between adjacent vertebral bodies and/or various portions of the spine (e.g., intervertebral disc, facets, spinous process) may be removed. For example, a fusion may be performed or may have been performed of the L5 and S1 vertebrae. The pedicle screw assembly 100 represents an embodiment of pre-existing hardware that could be used; other types of hardware could be used in other embodiments.

Figure 2:
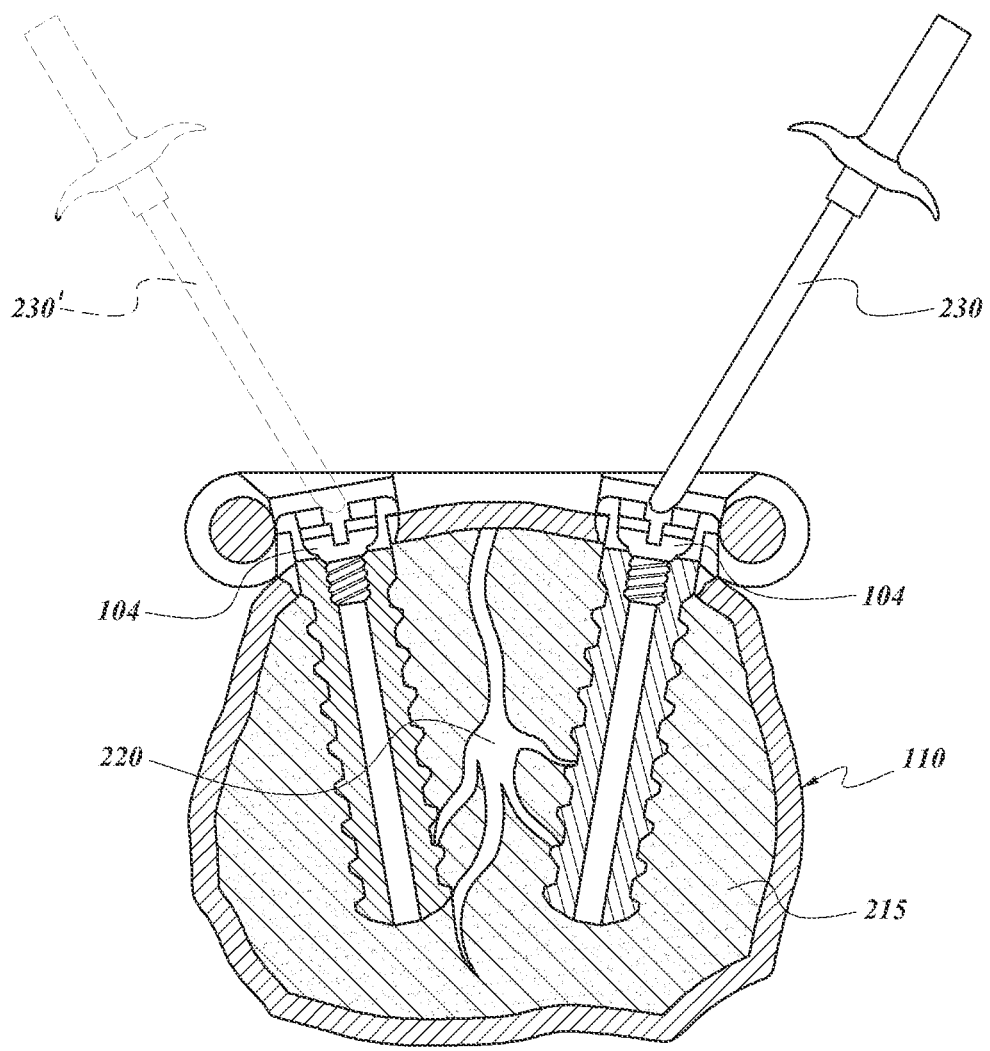
FIG. 2 illustrates pedicle screws inserted within a vertebral body of the spine and application of thermal energy to the pedicle screws.

FIG. 2 illustrates two pedicle screws 104 inserted within a vertebral body 110 of a human spine 102. A distal end of each of the pedicle screws 104 is located within an inner cancellous bone region 215 of the vertebral body 110. As shown in FIG. 2, a portion of a basivertebral nerve 220 may be located within the inner cancellous bone region 215 of the vertebral body 110. In several embodiments, the pedicle screws 104 comprise conductive material that is capable of conducting thermal energy (e.g., transferring heat) to the cancellous bone surrounding the pedicle screw, thereby heating the cancellous bone and at least a portion of the basivertebral nerve 220 located within the cancellous bone. For example, the conductive material may comprise one or more metals or alloys (e.g., copper, silver, gold, titanium, aluminum, brass, stainless steel) and/or conductive polymers (e.g., conductive silicone) or other conductive materials. The pedicle screws may be self-tapping screws.

In accordance with several embodiments of the invention, thermal energy may be applied to one or more pedicle screws (e.g., by an RF energy delivery instrument coupled to an RF generator). The thermal energy may be conducted by heat transfer to the surrounding cancellous bone, thereby heating up the cancellous bone. In accordance with several embodiments, the thermal energy is applied with a sufficient temperature and over a sufficient duration of time to heat the cancellous bone such that the basivertebral nerve extending through the cancellous bone of the vertebral body is modulated. In several embodiments, modulation comprises permanent ablation or denervation. In some embodiments, modulation comprises temporary denervation or inhibition. In some embodiments, modulation comprises stimulation. In some embodiments, thermal energy is applied to only one pedicle screw. In some embodiments, thermal energy is applied to multiple pedicle screws, either simultaneously or successively. In some embodiments, multiple levels of vertebral bodies are treated simultaneously or successively by application of thermal energy to pedicle screws or other bone fasteners. In one embodiment, a bipolar system is used to connect a first (e.g., active) electrode to a first pedicle screw and to connect a second (e.g., return) electrode to a second pedicle screw (e.g., to create an electrically conductive pathway between the first electrode and the second electrode). In one embodiment, a first alligator clip can be connected to a first pedicle screw and a second alligator clip can be connected to a second pedicle screw. The first pedicle screw may be on a first side of a vertebral body and the second pedicle screw may be on a second side of the vertebral body, with the first and second sides being defined by any path (e.g., line) extending through a general midpoint of the vertebral body. In one embodiment, the first and second sides are on opposite sides of a line substantially aligned with a spinous process connected to the vertebral body.

Thermal energy may be applied by a thermal energy delivery device 230 (e.g., a heating instrument, an electric or gas-fired iron similar to a soldering iron, a monopolar or bipolar electrode probe, etc.) Any energy delivery device capable of delivering energy can be used (e.g., RF energy delivery devices, microwave energy delivery devices, laser devices, infrared energy devices, other electromagnetic energy delivery devices, ultrasound energy delivery devices, and the like). In some embodiments, multiple energy delivery devices 230, 230' may optionally be used simultaneously at different locations (e.g., in conjunction with different bone fasteners at a single spine level or at different spine levels). In some embodiments, a single energy delivery device may have multiple members, branches, or extensions configured to apply energy at different locations. For example, a single energy delivery device may comprise a plurality of energy delivery members, such as multiple electrodes (either on a single continuous structure or on separate extensions or branches). The branches or extensions may be separately steerable or controllable (e.g., using pull wire, shape memory material, and/or active steering mechanisms). Pre-existing devices or implants within the vertebral body or other bone capable of conducting heat other than pedicle screws may also be used to conduct heat to bone tissue to modulate intraosseous nerves, such as staples, bone anchors or non-threaded bone fasteners.

Temperatures of the thermal energy applied to the pedicle screw or other bone fastener may range from about 70 to about 115 degrees Celsius (e.g., from about 70 to about 90 degrees Celsius, from about 75 to about 90 degrees Celsius, from about 80 to about 100 degrees Celsius, from about 85 to about 95 degrees Celsius, from about 90 to about 110 degrees Celsius, from about 95 to about 115 degrees Celsius, or overlapping ranges thereof). The time of treatment may range from about 10 seconds to about 1 hour (e.g., from 10 seconds to 1 minute, 1 minute to 5 minutes, from 5 minutes to 10 minutes, from 10 minutes to 20 minutes, from 15 minutes to 30 minutes, from 20 minutes to 40 minutes, from 30 minutes to 1 hour, from 45 minutes to 1 hour, or overlapping ranges thereof). Pulsed energy may be delivered according to several embodiments herein.

In some embodiments, a heating zone is established and controlled within a vertebral body so as not to heat any portion of the vertebral body within 1 cm of the posterior wall of the vertebral body. For example, a bone screw may include or be provided with insulating elements extending along the length from the exposed proximal end to the distal end with the distal end or tip being uninsulated, such that heat or energy is delivered to the vertebral body in a controlled manner. In some embodiments, the heating zone is maintained to a region that is between about 10% and about 80%, between about 5% and about 70%, between about 10% and about 65%, between about 20% and about 60%, between about 30% and about 55%, or overlapping ranges thereof, of the distance from the posterior wall to the anterior wall of the vertebral body. In one embodiment, the heating zone is configured to encompass a terminus of a basivertebral nerve.

Cooling may be provided to prevent surrounding tissues from being heated during the nerve modulation procedure. Cooling may be applied by circulating fluid through one or more lumens of an energy delivery device. The cooling may be provided by convective cooling or conductive cooling. The circulating fluid may be provided by a fluid source (e.g., reservoir) in fluid communication with the energy delivery device. Cooling may be provided by the same instrument used to deliver thermal energy (e.g., heat) to the pedicle screw or a separate instrument.

In some embodiments, cooling may be applied to the pedicle screw or other fastener for nerve modulation instead of heat (e.g., for cryotherapy applications). The temperature and duration of the cooling may be sufficient to modulate intraosseous nerves (e.g., ablation due to excessive cooling). Cooling may be provided by the same instrument used to deliver thermal energy (e.g., heat) to the pedicle screw or a separate instrument.

In some embodiments, a channel may be formed through the pedicle screw for delivery of one or more fluids or agents to the cancellous bone region. The channel may be formed by a device configured to bore through, drill through or puncture the pedicle screw. The agents delivered to the bone region may comprise bone morphogenetic proteins, for example. In some embodiments, the fluids or agents delivered to the bone region may comprise chemicals for modulating nerves (e.g., chemoablative agents, nerve-inhibiting agents, or nerve stimulating agents). In some embodiments, the bone screws or fasteners include a channel or lumen into which a heat or energy delivery probe or device may be inserted and advanced in order to deliver controlled heat or energy to the bone. In some embodiments, the bone screws or fasteners are fenestrated. For example, the bone screws or fasteners may have one or more holes or openings along at least a portion of the length of the bone screws or fasteners (e.g., for delivering liquid, gas, or solid materials to a target location).

In some embodiments, tumors or bone metastases within the vertebral body or other bones in which the pedicle screw is inserted may be targeted by delivering thermal energy via the pedicle screw or by delivering therapeutic agents (e.g., chemotherapy agents) through a channel or lumen formed or previously existing in the pedicle screw or other bone fastener. In some embodiments, the thermal energy is delivered using the pedicle screw and the therapeutic agents are delivered without use of the pedicle screw.

In some embodiments, fractures within the bone surrounding the pedicle screws or other bone fasteners may be treated by applying heat or energy or delivering agents or bone filler material to the bone. For example, bone morphogenetic proteins and/or bone cement may be delivered in conjunction with vertebroplasty or other procedures to treat fractures or promote bone growth or bone healing. In some embodiments, the energy is applied using the pedicle screw and the agents and/or bone filler material is delivered using standard delivery instruments (with or without use of the pedicle screw). In some embodiments, vertebral compression fractures (which may be caused by osteoporosis or cancer) are treated in conjunction with energy delivery using the pedicle screw to modulate nerves to treat back pain.

In some embodiments, nerve modulation is performed in conjunction with (e.g., contemporaneous with) spinal fusion or other spinal stabilization procedures. A stabilization assembly including pedicle screws or other bone fasteners may be affixed or connected to a portion of the spine and then thermal energy may be applied to one or more of the pedicle screws to heat up the inner cancellous bone region sufficient to modulate the nerves. The methods may be performed on thoracic, lumbar, cervical or sacral vertebrae, or a combination thereof. The methods may be performed on vertebral levels or segments that are difficult to access via a percutaneous approach. In one embodiment, a fusion procedure may have been performed to fuse the L5 and S1 vertebrae. Nerve modulation may be performed contemporaneously or post-facto using one or more pedicle screws or other bone fasteners implanted or otherwise inserted within one or more vertebral bodies.

In accordance with several embodiments, the methods of facilitating neuromodulation of intraosseous nerves described herein are performed without requiring knowledge of the exact location of the intraosseous nerve and without forming additional channels or passageways or incisions in bone to access the intraosseous nerve. For example, the methods described herein do not require any particular approach or curved instruments to be used to facilitate neuromodulation. The methods described herein facilitate neuromodulation with devices previously existing within the bone (e.g., hardware inserted during previous procedures).

In accordance with several embodiments, the systems and methods of treating back pain or facilitating neuromodulation of intraosseous nerves described herein can be performed without surgical resection, without general anesthesia, and/or with virtually no blood loss. In some embodiments, the systems and methods of treating back pain or facilitating neuromodulation of intraosseous nerves described herein facilitate easy retreat if necessary. In accordance with several embodiments of the invention, successful treatment can be performed in challenging or difficult-to-access locations and access can be varied depending on bone structure. One or more of these advantages also apply to treatment of tissue outside of the spine (e.g., other orthopedic applications or other tissue).

While the embodiments are susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "applying thermal energy" include "instructing the applying of thermal energy."

Various embodiments of the invention have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. For example, description of a range such as from 70 to 115 degrees should be considered to have specifically disclosed subranges such as from 70 to 80 degrees, from 70 to 100 degrees, from 70 to 110 degrees, from 80 to 100 degrees etc., as well as individual numbers within that range, for example, 70, 80, 90, 95, 100, 70.5, 90.5 and any whole and partial increments therebetween. Language such as "up to," "at least," "greater than," "less than," "between," and the like includes the number recited. Numbers preceded by a term such as "about" or "approximately" include the recited numbers. For example, "about 10%" includes "10%." For example, the terms "approximately", "about", and "substantially" as used herein represent an amount close to the stated amount that still performs a desired function or achieves a desired result.

What is claimed is:

1. A method of treating back pain of a subject, the method comprising: performing a nerve ablation procedure within at least one of two adjacent vertebral bodies that have been fused together in a prior spinal fusion procedure separate from the nerve ablation procedure, wherein at least two pedicle screws are inserted within the at least one of the two adjacent vertebral bodies during the spinal fusion procedure; wherein the nerve ablation procedure comprises: applying thermal energy to create a controlled heating zone sufficient to ablate a basivertebral nerve within the at least one of the two adjacent vertebral bodies that have been fused together, wherein the controlled heating zone encompasses a terminus of the basivertebral nerve, wherein applying thermal energy comprises conducting energy through the at least two pedicle screws to ablate the basivertebral nerve, wherein the thermal energy is applied as bipolar radiofrequency energy using at least one radiofrequency energy delivery device, and wherein the thermal energy is applied for a period of 5 to 10 minutes at a temperature between 70 degrees Celsius and 90 degrees Celsius.

2. The method of claim 1,
   wherein the two adjacent vertebral bodies are vertebral bodies of an L5 vertebra and an S1 vertebra, wherein the at least one radiofrequency energy delivery device comprises an active electrode and a return electrode, and wherein the thermal energy is generated by a radiofrequency generator.

3. The method of claim 1, wherein the two adjacent vertebral bodies are vertebral bodies of an L5 vertebra and an S1 vertebra.

4. The method of claim 1, wherein the two adjacent vertebral bodies are vertebral bodies of lumbar vertebrae.

5. The method of claim 1, wherein the two adjacent vertebral bodies are vertebral bodies of sacral vertebrae.

6. The method of claim 1, further comprising circulating cooling fluid through the at least one radiofrequency energy delivery device.

7. The method of claim 1, wherein the thermal energy is applied using two radiofrequency energy delivery devices inserted within the at least one of the two adjacent vertebral bodies.

8. The method of claim 1, wherein the thermal energy is applied using two radiofrequency energy delivery devices, with one of the two radiofrequency energy delivery devices being inserted within the at least one of the two adjacent vertebral bodies.

9. The method of claim 1, wherein the thermal energy is generated by a radiofrequency generator.

10. A method of treating back pain of a subject, the method comprising: performing a nerve ablation procedure within at least one of two adjacent vertebral bodies that have been fused together in a prior spinal fusion procedure separate from the nerve ablation procedure, wherein at least one pedicle screw is inserted into the at least one of the two adjacent vertebral bodies during the spinal fusion procedure; wherein the nerve ablation procedure comprises: applying thermal energy from an energy delivery device, wherein the energy delivery device comprises at least one radiofrequency energy delivery device, wherein the thermal energy is applied for a period of 10 to 20 minutes at a temperature between 70 degrees Celsius and 90 degrees Celsius with a sufficient temperature and over a sufficient duration of time to create a controlled heating zone within cancellous bone within the at least one of the two adjacent vertebral bodies sufficient to ablate a terminus of a basivertebral nerve within the at least one of the two adjacent vertebral bodies, wherein applying thermal energy comprises conducting energy through the at least one pedicle screw to ablate the basivertebral nerve, and wherein the nerve ablation procedure further comprises providing cooling during the nerve ablation procedure.

11. The method of claim 10:

wherein the at least one radiofrequency energy delivery device comprises a radiofrequency probe having an active electrode and a return electrode.

12. The method of claim 10, wherein the two adjacent vertebral bodies are vertebral bodies of an L5 vertebra and an S1 vertebra.

13. The method of claim 10, wherein the two adjacent vertebral bodies are vertebral bodies of lumbar vertebrae.

14. The method of claim 10, wherein the two adjacent vertebral bodies are vertebral bodies of sacral vertebrae.

15. The method of claim 10, wherein providing cooling comprises circulating cooling fluid through the at least one radiofrequency energy delivery device.

16. A method of treating back pain of a subject, the method comprising: performing a nerve ablation procedure within at least one of two adjacent vertebral bodies that have been fused together in a prior spinal fusion procedure separate from the nerve ablation procedure, wherein at least one pedicle screw is inserted into the at least one of the two adjacent vertebral bodies during the spinal fusion procedure; and wherein the nerve ablation procedure comprises: ablating a terminus of a basivertebral nerve within the at least one of the two adjacent vertebral bodies performed by applying thermal energy, wherein applying thermal energy comprises conducting energy through the at least one pedicle screw to ablate the basivertebral nerve, wherein the thermal energy is applied for a period of 5 to 10 minutes at a temperature between 70 degrees Celsius and 90 degrees Celsius.

17. The method of claim 16, wherein ablating the basivertebral nerve is performed by applying thermal energy using a radiofrequency energy delivery device.

18. The method of claim 16, wherein ablating the basivertebral nerve is performed by applying thermal energy using an energy delivery device, wherein the energy delivery device is selected from the group consisting of: a microwave energy delivery device, a laser device, an infrared energy device, and an ultrasound energy delivery device.

* * * * *